United States Patent
Mangiardi

(10) Patent No.: US 11,051,958 B2
(45) Date of Patent: Jul. 6, 2021

(54) BIODEGRADABLE SUPPORTING DEVICE

(71) Applicant: Q3 MEDICAL DEVICES LIMITED, Dublin (IE)

(72) Inventor: Eric K. Mangiardi, Charlotte, NC (US)

(73) Assignee: Q3 MEDICAL DEVICES LIMITED, Dublin (IE)

( * ) Notice: Subject to any disclaimer, the term of this patent is extended or adjusted under 35 U.S.C. 154(b) by 0 days.

(21) Appl. No.: 15/164,683

(22) Filed: May 25, 2016

(65) Prior Publication Data

US 2016/0262915 A1  Sep. 15, 2016

Related U.S. Application Data

(63) Continuation-in-part of application No. 14/826,732, filed on Aug. 14, 2015, which is a continuation of application No. 14/174,600, filed on Feb. 6, 2014, now Pat. No. 9,149,565, which is a continuation of application No. 13/416,074, filed on Mar. 9, 2012, now Pat. No. 8,834,902.

(51) Int. Cl.
| | |
|---|---|
| *A61F 2/844* | (2013.01) |
| *A61F 2/90* | (2013.01) |
| *A61L 31/16* | (2006.01) |
| *A61L 31/08* | (2006.01) |
| *A61L 31/02* | (2006.01) |
| *A61L 31/10* | (2006.01) |
| *A61L 31/00* | (2006.01) |
| *A61K 31/436* | (2006.01) |
| *A61K 31/337* | (2006.01) |
| *A61F 2/86* | (2013.01) |
| *A61L 31/14* | (2006.01) |
| *A61B 17/12* | (2006.01) |
| *A61F 2/07* | (2013.01) |
| *A61F 2/82* | (2013.01) |
| *A61B 17/00* | (2006.01) |
| *A61F 2/915* | (2013.01) |
| *B82Y 5/00* | (2011.01) |

(52) U.S. Cl.
CPC .......... *A61F 2/844* (2013.01); *A61B 17/0057* (2013.01); *A61B 17/12113* (2013.01); *A61F 2/07* (2013.01); *A61F 2/82* (2013.01); *A61F 2/86* (2013.01); *A61F 2/90* (2013.01); *A61F 2/915* (2013.01); *A61K 31/337* (2013.01); *A61K 31/436* (2013.01); *A61L 31/005* (2013.01); *A61L 31/022* (2013.01); *A61L 31/088* (2013.01); *A61L 31/10* (2013.01); *A61L 31/14* (2013.01); *A61L 31/148* (2013.01); *A61L 31/16* (2013.01); *A61B 17/12109* (2013.01); *A61B 2017/00588* (2013.01); *A61B 2017/00592* (2013.01); *A61B 2017/00632* (2013.01); *A61F 2002/91575* (2013.01); *A61F 2002/91583* (2013.01); *A61F 2210/0004* (2013.01); *A61F 2210/0009* (2013.01); *A61F 2210/0076* (2013.01); *A61F 2230/0069* (2013.01); *A61F 2250/003* (2013.01); *A61F 2250/0067* (2013.01); *A61F 2310/00041* (2013.01); *A61F 2310/00065* (2013.01); *A61L 2300/416* (2013.01); *A61L 2300/64* (2013.01); *A61L 2400/12* (2013.01); *A61L 2420/02* (2013.01); *A61L 2420/04* (2013.01); *A61L 2420/08* (2013.01); *B82Y 5/00* (2013.01)

(58) Field of Classification Search
CPC .......... A61B 17/0057; A61B 17/12109; A61B 17/12113; A61B 2017/00588; A61B 2017/00592; A61F 2009/91583; A61F 2210/0004; A61F 2210/0076; A61F 2230/0069; A61F 2250/003; A61F 2250/0067; A61F 2310/00041; A61F 2009/91575; A61F 2002/91583; A61F 2330/0069; A61F 2/07; A61F 2/915
See application file for complete search history.

(56) References Cited

U.S. PATENT DOCUMENTS

| | | | |
|---|---|---|---|
| 4,642,104 A | 2/1987 | Sakamoto et al. | |
| 5,653,745 A | 8/1997 | Trescony et al. | |
| 6,569,195 B2 | 5/2003 | Yang et al. | |
| 7,527,644 B2 * | 5/2009 | Mangiardi | A61F 2/91 623/1.15 |
| 2003/0040754 A1 | 2/2003 | Mitchell et al. | |
| 2004/0030377 A1 | 2/2004 | Dubson et al. | |

(Continued)

FOREIGN PATENT DOCUMENTS

| | | | |
|---|---|---|---|
| CN | 104287870 | 1/2015 | |
| DE | WO2010/145842 | * 12/2010 | ............. A61L 27/04 |

OTHER PUBLICATIONS

Wu (Journal of the Mechanical Behavior of Biomedical Materials 8 (2012) 1-7). (Year: 2012).*

(Continued)

*Primary Examiner* — Anna R Falkowitz
(74) *Attorney, Agent, or Firm* — Ping Wang; Morris, Manning & Martin LLP

(57) ABSTRACT

A biodegradable in vivo supporting device is disclosed. In one embodiment, a coated stent device includes a biodegradable metal alloy scaffold made from a magnesium alloy, iron alloy, zinc alloy, or combination thereof, and the metal scaffold comprises a plurality of metal struts. The metal struts are at least partially covered with a biodegradable polymer coating. A method for making and a method for using a biodegradable in vivo supporting device are also disclosed.

19 Claims, 4 Drawing Sheets

(56) References Cited

U.S. PATENT DOCUMENTS

| | | | |
|---|---|---|---|
| 2006/0229711 A1* | 10/2006 | Yan | A61F 2/02 623/1.38 |
| 2007/0043433 A1 | 2/2007 | Chandrasekaran | |
| 2007/0050009 A1 | 3/2007 | Flanagan | |
| 2007/0135908 A1* | 6/2007 | Zhao | A61L 31/022 623/1.46 |
| 2007/0270939 A1 | 11/2007 | Hood et al. | |
| 2008/0319536 A1 | 12/2008 | Houston et al. | |
| 2010/0034960 A1 | 2/2010 | Kindaichi et al. | |
| 2010/0076544 A1 | 3/2010 | Hoffmann et al. | |
| 2010/0076556 A1* | 3/2010 | Tomantschger | A61L 17/10 623/11.11 |
| 2011/0160833 A1* | 6/2011 | Gonzalez | A61F 2/07 623/1.11 |
| 2011/0307053 A1 | 12/2011 | Gale et al. | |
| 2012/0143318 A1* | 6/2012 | Gulcher | A61L 27/047 623/1.46 |
| 2012/0238806 A1* | 9/2012 | Mangiardi | A61F 2/958 600/106 |
| 2014/0147575 A1 | 5/2014 | Mangiardi | |
| 2014/0356407 A1 | 12/2014 | Mangiardi | |
| 2015/0352262 A1 | 12/2015 | Mangiardi | |

OTHER PUBLICATIONS

International Search Report of Application No. PCT/US2016/034183, dated Aug. 31, 2016.
International Search Report and Written Opinion issued in International Patent Application No. PCT/US2012/028448 dated Nov. 23, 2012.
McGovren, "Chapter 2: Pharmacologic Principles," Cancer Chemotherapy Handbook, 2nd Edition, 1994, pp. 15-34.
File history of U.S. Appl. No. 13/416,074, filed Mar. 9, 2012.
File history of U.S. Appl. No. 14/174,600, filed Feb. 6, 2014.
European Search Report issued in European Application 09842845.1 dated Nov. 19, 2014.
Supplementary European Search Report of Application No. EP 12 87 0570 dated Sep. 1, 2015.
File history of U.S. Appl. No. 14/826,732, filed Aug. 14, 2015.

* cited by examiner

US 11,051,958 B2

BIODEGRADABLE SUPPORTING DEVICE

This application is a continuation-in-part application of U.S. patent application Ser. No. 14/826,732, filed on Aug. 14, 2015, which is a continuation application of U.S. patent application Ser. No. 14/174,600, filed on Feb. 6, 2014, now U.S. Pat. No. 9,149,565, which is a continuation application of U.S. patent application Ser. No. 13/416,074, filed on Mar. 9, 2012, now U.S. Pat. No. 8,834,902. The entirety of the aforementioned applications is incorporated herein by reference.

FIELD

The present application generally relates to medical devices and, in particular, to biodegradable in vivo supporting devices, such as coated stents.

BACKGROUND

In vivo supporting devices or barrier devices, such as stents, is a man-made "tube" or "frame" inserted into a natural passage or conduit in the body to prevent, or counteract, a disease-induced, localized flow constriction or flow outflow like a leak or aneurysm. Supporting devices include vascular supporting devices, non-vascular supporting devices, and heart failure closure or aneurysm sealing devices. Vascular supporting devices are designed for applications in the vascular system, such as arteries and veins. Non-vascular supporting devices are used in other body lumens such as biliary, colorectal, esophageal, ureteral and urethral tract, and upper airway. Closure devices may be used to correct heart defects, such as atrial septal defects (ASDs), patent foramen ovales (PFOB) and ventricular septal defect (VSDs). Aneurysm sealing devices may be used to close off potentially dangerous aneurysms or pseudo aneurysms throughout the vascular and non-vascular systems.

In vivo supporting devices are typically made from a rigid material, such as a metal, alloy or rigid polymeric material. The supporting device may be made from a biodegradable material so that there is no need to remove the device after the correction of the underline defects. A common problem with the biodegradable supporting device, however, is that the device may disintegrate in an uncontrolled manner and break into large pieces which, if entering the circulation of a body fluid such as blood, may interfere with the normal circulation of the body fluid. Therefore, there exists a need for improved in vivo supporting devices that are biodegradable in a controlled manner.

SUMMARY

One aspect of the present application relates to a biodegradable in vivo supporting device. The device comprises a biodegradable metal alloy scaffold made from a magnesium alloy, an iron alloy, a zinc alloy, or combination thereof, the metal scaffold comprising a plurality of metal struts. The device also comprises a biodegradable polymer coating at least partially covering the metal struts. In some embodiments, the metal struts have an average cross-sectional thickness between 100-200 µm, the polymer coating has a thickness between 10-100 µm.

Another aspect of the present application relates to a method for producing a biodegradable in vivo supporting device. The method comprises the steps of (a) producing a biodegradable metal scaffold from a magnesium alloy, an iron alloy, a zinc alloy, or combination thereof, wherein the metal scaffold is configured for use in a stent and comprises a plurality of metal struts having an average cross-sectional thickness between 100-200 µm, and (b) coating the biodegradable metal scaffold with a biodegradable polymer coating wherein the biodegradable polymer coating comprises one or more polymeric layers, and wherein the polymer coating has a thickness between 10-100 µm.

Yet another aspect of the present application relates to a method for treating a condition in a subject with the biodegradable in vivo supporting device. The method comprises the steps of establishing an entry portal into a body lumen in a subject in need of such treatment; delivering said supporting device to a target location through said body lumen; and deploying said supporting device at said target location.

BRIEF DESCRIPTION OF DRAWINGS

The present application can be better understood by reference to the following drawings, wherein like references numerals represent like elements. The drawings are merely exemplary to illustrate certain features that may be used singularly or in combination with other features and the present invention should not be limited to the embodiments shown.

FIG. 4A shows a partially covered stent strut with exposed middle section. FIG. 4B shows a partially covered stent strut with exposed end section. FIG. 4C shows a stent strut with multiple exposed sections.

FIGS. 5A and 5B show a perspective view and a cross-sectional view, respectively, of a stent strut covered with a biodegradable layer on the outer surface. FIGS. 5C, 5D and 5E show a perspective view and cross-sectional views of another stent strut partially covered with a biodegradable layer. FIG. 5F shows the perspective view of a strut with a coating that covers less than half of the strut outer surface.

DETAILED DESCRIPTION

Figure 1:
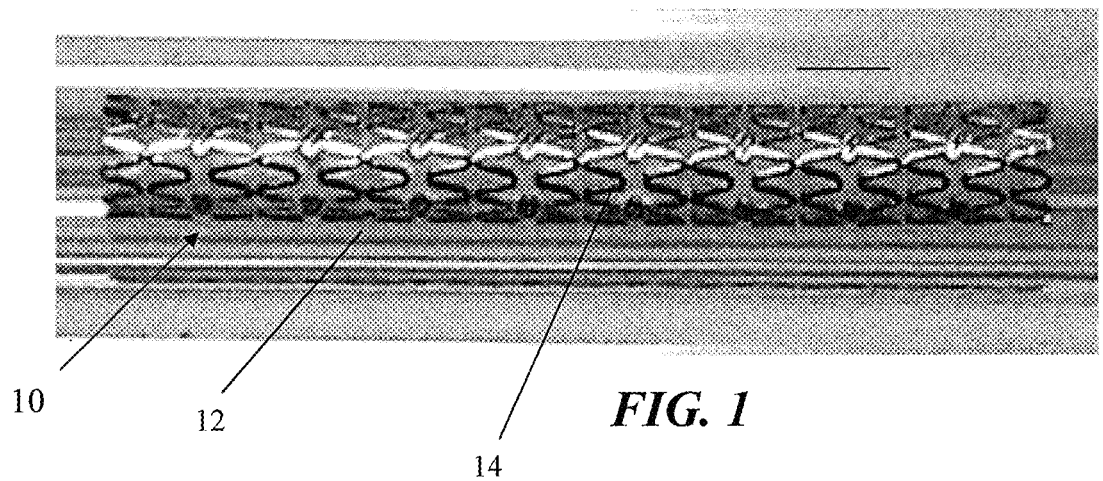
FIG. 1 shows an embodiment of a stent with very thin struts.

The present application will employ, unless otherwise indicated, conventional medical devices and methods within the skill of the art. Such techniques are explained fully in the literature. All publications, patents and patent applications cited herein, whether supra or infra, are hereby incorporated by reference in their entirety.

One aspect of the present application relates to a biodegradable in vivo supporting device, or coated stent device. The device comprises a body formed with a biodegradable metal scaffold coated with a biodegradable polymer coating. As used herein, the term "biodegradable" means that both the metal stent and the polymer coating degrade or decompose in a physiological environment, such as the vascular system of a human or animal body, typically within weeks or months, so that the supporting device loses its integrity and is broken down into components that are metabolizable or excretable. In addition, the device is biocompatible and contains non-toxic levels of metallic and polymeric materials.

In certain embodiments, the device is gradually degraded until the function of the device is no longer physiologically appropriate and/or necessary. The polymer coating covering the metal scaffold may be engineered to speed up or slow down the course of biodegradation relative to the underlying metal scaffold, which degrades at a different rate. Preferably, the polymer coating and metal scaffold degrade and become absorbed in situ at the treatment site, such that the device becomes completely degraded and loses its integrity only when the traumatized tissue of the vessel has healed and the device is no longer needed in the vascular lumen. Thus, the biodegradable device may serve a temporary function in the body, such as supporting a lumen or drug delivery.

The acceptable non-toxic limits and the acceptable time frame for degradation can vary and can depend on particular physical and physiological characteristics of the patient, the particular in vivo site of the implantation device, and the particular medical use of the implantation device.

The In Vivo Supporting Device

Exemplary biodegradable in vivo supporting devices include, but are not limited to, vascular supporting devices, such as vascular stents, non-vascular stents, non-vascular supporting devices, closure/sealing/barrier devices, such as devices for correcting heart defects, including atrial septal defects (ASDs), patent foramen ovales (PFOs) and ventricular septal defects (VSDs), as well as devices for sealing fistulas and aneurysms. As used herein, the term "stent" refers to a device which is implanted within a bodily lumen to hold open the lumen or to reinforce a small segment of the lumen. Stents can be used for treating obstructed vessels, biliary ducts, pancreatic ducts, ureters, or other obstructed lumens, fractured canals, bones with hollow centers and/or for delivering various drugs through controlled release to the particular lumen of interest.

The shape, length and diameter of the in vivo supporting device are application dependent. Each type of the in vivo supporting device is designed to fit within a specific part of the anatomy. Therefore, the shape, length, and diameter of the supporting devices differ by type to accommodate and support different sized lumens and different clinical needs. For example, each major stent application, such as vascular, pancreatic, ureteral, or metacarpal canal, and other hollow bone structures, requires a different diameter and shape to enable placement, to remain in place after placement, to stabilize and support the anatomy it is placed in, and to allow conformance to the normal anatomy. Most stents have a tubular body, which are further defined by an enclosed or open channel allowing a body fluid to flow though the stent in a body lumen. In certain embodiments, a stent body may further include a center lumen to accommodate a guide wire. This center lumen may provide additionally flow throughput after the removal of guide wire.

As used herein, the term "cross-sectional thickness" in reference to a strut of the device refers to the distance between points on opposite sides of the strut that lay on a line that is perpendicular to and passes through the longitudinal centerline of the device. Alternatively, the thickness of a strut can be defined in terms of its "maximal thickness, which refers to the distance between two points that are farthest away from each other in a cross-section of the strut that is perpendicular to the longitudinal centerline of the device. In some embodiments, a thickness measurement may refer to the thickness of the metal scaffold portion of the strut alone, the polymer coating alone, or the combined total of the polymer coating and the metal scaffold.

In certain embodiments, the diameter of an in vivo supporting device may be defined by the width across the shaft of the device body. In one embodiment, the device has a uniform diameter along the length of its body. In another embodiment, the device has a variable diameter along the length of its body. In one embodiment, the device has a tubular body with a distal end, a proximal end and a middle section, wherein the diameter at the distal end is smaller than the diameter at the proximal end. In another embodiment, the diameter at the proximal end is smaller than the diameter at the distal end. In yet another embodiment, the diameters at the distal end and the proximal end are both smaller than the diameter at the middle section of the device. In a particular embodiment, the device is a stent with an elongated tubular body having a distal end, a proximal end and a middle section, and at least one channel formed on or in the body to provide fluid communication between the proximal and distal ends.

One aspect of the present application relates to a biodegradable in vivo supporting device comprising: a biodegradable metal alloy scaffold made from a magnesium alloy, an iron alloy, a zinc alloy, or combination thereof, the metal scaffold comprising a plurality of metal struts; a biodegradable polymer coating at least partially covering the metal struts; wherein the metal struts have an average cross-sectional thickness between 100-200 μm, the polymer coating has a thickness between 10-100 μm.

In some embodiments, the alloy further comprises one or more metals selected from the group consisting of manganese, magnesium, iron, zinc, palladium, cobalt, aluminum, tungsten, boron, carbon, sulfur, silicon, lithium, zirconium, calcium, and yttrium.

In other embodiments, the metal alloy further comprises at least one rare earth metal and a majority of the metal alloy comprises magnesium. In further embodiments, the rare earth metal is neodymium, cerium or yttrium.

In some embodiments, the biodegradable metal scaffold is made from a magnesium alloy having at least 96 wt. % of magnesium, at least 1 wt. % of manganese, and at least 0.5 wt. % of a rare earth metal. In some further embodiments, the biodegradable metal scaffold is made from a magnesium alloy having a magnesium content of 96-97.9 wt. %, a manganese content of 1.6-2 wt. %, and rare earth metal content of 0.5-2 wt. %. In other further embodiments, the biodegradable metal scaffold is made from a magnesium alloy having a magnesium content of 97.45 wt. %, a manganese content of 1.8 wt. %, and a neodymium content of 0.75 wt. %.

In some embodiments, the biodegradable polymer coating has one or more holes allowing direct contact between the metal struts and body fluids when the stent device is placed inside a body lumen.

In other embodiments, the biodegradable polymer coating partially covers the metal struts but does not cover openings between the struts.

In still other embodiments, the biodegradable polymer coating covers exterior surfaces of the metal scaffold and openings between the metal struts.

In some embodiments, the biodegradable polymer coating comprises an anti-proliferative agent selected from the group consisting of paclitaxel, sirolimus, docetaxel, biolimus A9, zotarolimus, everolimus, myolimus, novolimus, pimecrolimus, tacrolimus, ridaforolimus, temsirolimus and combination thereof.

In particular embodiments, the biodegradable metal scaffold is an expandable scaffold. In further embodiments, the expandable scaffold is balloon-expandable. In other further embodiments, the expandable scaffold is a self-expandable scaffold that expands after implantation. In still other further embodiments, the biodegradable polymer coating is an elastic coating that expands with the biodegradable metal scaffold. In yet other further embodiments, the biodegradable polymer coating forms fissures upon expansion of the biodegradable metal scaffold in vivo. In some even further embodiments, the biodegradable polymer coating is permeable to body fluid.

In some embodiments, the metal scaffold is less than 60% w/w or less than 60% v/v of the device.

In particular embodiments, the biodegradable polymer comprises PLLA, PLGA, or a combination thereof.

In some embodiments, the device further comprises an additional coating between the metal alloy scaffold and the biodegradable coating that delays the degradation time of the metal alloy scaffold. In some further embodiments, the additional coating is a nano-coating of iron.

In some embodiments, the biodegradable polymer coating comprises stem cells.

In other embodiments, the biodegradable polymer coating further comprises metal particles in an amount sufficient for visualizing the device during implantation. In some further embodiments, the metal particles are selected from the group consisting of iron, magnesium, tantalum, zinc and alloys thereof.

In particular embodiments, the biodegradable polymer is an elastic coating that allows the device to be used in non-conforming lesions.

Another aspect of the present application relates to a method for producing a biodegradable in vivo supporting device, comprising: (a) producing a biodegradable metal scaffold from a magnesium alloy, an iron alloy, a zinc alloy, or combination thereof, wherein the metal scaffold comprises a plurality of metal struts having an average cross-sectional thickness between 100-200 µm, and (b) coating the biodegradable metal scaffold with a biodegradable polymer coating so that the metal scaffold is less than 60% w/w or less than 60% v/v of the device, wherein the biodegradable polymer coating comprises one or more polymeric layers, and wherein the polymer coating has a thickness between 10-100 µm. In some embodiments, the supporting device is configured for use in a stent or as a stent.

In some embodiments, the biodegradable polymer coating comprises an agent that prevents or reduces the post-implantation hyperplastic response.

Another aspect of the present application relates to a method for treating a condition in a subject with a biodegradable in vivo supporting device comprising: a biodegradable metal alloy scaffold made from a magnesium alloy, an iron alloy, a zinc alloy, or combination thereof, the metal scaffold comprising a plurality of metal struts; a biodegradable polymer coating at least partially covering the metal struts; wherein the metal struts have an average cross-sectional thickness between 100-200 µm, the polymer coating has a thickness between 10-100 µm. The method comprises establishing an entry portal into a body lumen in a subject in need of such treatment, delivering the supporting device to a target location through said body lumen, and deploring the supporting device at the target location.

The Biodegradable Metal Scaffold

The metal scaffold can be made from one or more biodegradable metals or metal alloys. As used herein, the term "metal" refers to both single element "pure" metals and metal alloys. Preferred metals include those that are naturally found in the human body, such as nutrients or trace metals that act as e.g., enzymatic cofactors. Exemplary metals include, but are not limited to, magnesium, iron, zinc, tungsten, manganese, calcium, lithium, molybdenum, selenium, copper, zirconium, chromium, strontium, beryllium, niobium, sodium, aluminum, potassium, titanium, vanadium, selenium, cobalt, nickel, boron, copper, gallium, silicon, ruthenium, rhodium, palladium, silver, indium, tin, praseodymium, tantalum, rhenium, platinum, gold, lead; rare earth metals, such as scandium, yttrium, lanthanum, cerium, neodymium, promethium, samarium, europium, gadolinium, terbium, dysprosium, holmium, erbium, thulium, ytterbium and lutetium; and alloys thereof.

In certain preferred embodiments, the biodegradable metal scaffold is made from a metal alloy. The addition of alloying elements provides an effective means for improving both mechanical properties and corrosion resistance. Metal alloys containing a combination of metallic materials can be designed to provide pre-determined decomposition profile in the body, typically within a period of several weeks or months, as appropriate, to form harmless constituents at non-toxic levels. Binary alloys (two constituents), ternary alloys (three constituents), quaternary alloys (four constituents) or quinary alloys (five constituents) of the above described metals may be employed in the biodegradable metal scaffold.

In some embodiments, the metal alloy has an average grain size of 20 µm or less, 15 µm or less, 10 µm or less, 7.5 µm or less, 5 µm or less, 4 µm or less, 3 µm or less, 2 µm or less, or 1 µm or less. In other embodiments, the average grain size is between 0.1 µm and 10 µm, between 0.5 µm and 5 µm, or between 1 µm and 4 µm.

To obtain uniform corrosion, the alloy may comprise a component, such as magnesium, titanium, zirconium, niobium, tantalum, zinc or silicon, which is covered with a protective oxide coat. A second component, which is soluble in blood or interstitial fluids, such as lithium sodium, potassium, calcium, iron or manganese may be added to the alloy to achieve uniform dissolution of the oxide coat. The corrosion rate can be regulated through the ratio of these two components.

Typically, the main component of the metal alloy is made up of either magnesium, iron, or zinc, and a minority (typically less than 10%) is made up of one or more metals, including manganese, magnesium, zinc, zirconium, calcium, and/or one or more rare earth metals. Rare earth metals may contribute to the mechanical strength and/or corrosion resistance of the metal alloy. Calcium may be used in a low quantity to prevent oxidation during the casting of the alloy. Zirconium may act as a grain refiner and may be used for improved mechanical properties.

The "main component" or "main constituent" in an alloy is present in the largest amount by weight. The amount of the main component is preferably at least 50%, at least 60%, at least 70%, at least 80%, at least 90%, at least 93%, at least 94%, at least 95%, at least 96%, at least 97% or at least 98% (w/w) of the metal scaffold. A "minor component" or "minor constituent" in the metal alloy refers to metallic materials, such as alloying elements, which are present in minor amounts by weight, individually or collectively, typically, less then 50%, less than 40%, less than 30%, less than 20%, less than 10%, less than 7%, less than 6%, less than 5%, less than 4%, less than 3%, less than 2%, less than 1%, or less than 0.5% (w/w) of the metal scaffold. The amount of each component in the alloy can vary and are selected so that the components in the resulting alloy are within acceptable non-toxic limits and degrade over an acceptable period of time.

In certain preferred embodiments, particularly where magnesium is the major component of the metal scaffold, one or more rare earth metals may be included. Rare earth metals and minor metal components may be included in the alloy, individually or collectively, in an amount between 0.2-10 wt. %, 0.2-5 wt. %, 0.2-2 wt. %, 0.2-1 wt. %, 0.5-10 wt. %, 0.5-5 wt. %, 0.5-2 wt. %, 0.5-1.5 wt. %, 0.5-1 wt. %, 1-5 wt. %, 1-2 wt. % or 1.5-2 wt. %.

Preferably, the alloy is composed so that the corrosion products form soluble salts, such as sodium, potassium, calcium, iron or zinc salts, or non-soluble colloidal particles comprising titanium, tantalum or niobium oxide. In addition, the corrosion rate may be adjusted so that gases, including hydrogen generated during the corrosion of lithium, sodium, potassium, magnesium, calcium or zinc, dissolve physically without forming macroscopic gas bubbles.

The biodegradable metal scaffold may further comprise one or more metal salts. Examples of metal salts include, but are not limited to salts of the following acids: sulfuric acid, sulfonic acid, phosphoric acid, nitric acid, nitrous acid, perchloric acid, hydrobromic acid, hydrochloric acid, formic acid, acetic acid, propionic acid, succinic acid, oxalic acid, gluconic acid, (glyconic acid, dextronic acid), lactic acid, malic acid, tartaric acid, tartronic acid (hydroxymalonic acid, hydroxypropanedioic acid), fumaric acid, citric acid, ascorbic acid, maleic acid, malonic acid, hydroxymaleic acid, pyruvic acid, phenylacetic acid, (o-, m-, p-) toluic acid, benzoic acid, p-aminobenzoic acid, p-hydroxybenzoic acid, salicylic acid, p-aminosalicylic acid, methanesulfonic acid, ethanesulfonic acid, hydroxyethanesulfonic acid, ethylenesulfonic acid, p-toluenesulfonic acid, naphthylsulfonic acid, naphthylaminesulfonic acid, sulfanilic acid, camphorsulfonic acid, china acid, quinic acid, o-methyl-mandelic acid, hydrogen-benzenesulfonic acid, methionine, tryptophan, lysine, arginine, picric acid (2,4,6-trinitrophenol), adipic acid, d-o-tolyltartaric acid, glutaric acid.

In some embodiments, the metal scaffold comprises a polymer mixed with particles of iron, magnesium, tantalum, zinc, other absorbable metals, or alloys thereof to enhance characteristics of expansion and resistance to compression. In some related embodiments, the particles are nanoparticles.

In some embodiments, the biodegradable metal scaffold is made from a magnesium alloy. Metals to be include in the magnesium alloys may be preferably selected from the groups consisting of manganese, zinc, aluminum, zirconium, neodymium, yttrium and silver.

In some embodiments, the metal alloy comprises neodymium. After deployment, the neodymium-containing metal alloy is degraded based on surface erosion. Briefly, the surface of the neodymium-containing metal alloy oxidizes and forms an oxidized layer, which dissipates over time, exposing the un-oxidized alloy under the oxidized layer. The un-oxidized alloy is then oxidized to form another oxidized layer and goes through the same cycle until the whole metal scaffold dissipates. Depending on the size and composition of the metal scaffold, this degradation process may last from several months to a year, thus allowing a gradual degradation of the supporting device.

In some embodiments, the neodymium-containing alloy is a high-strength permanent magnet that provides low magnet mass (or volume) and/or strong magnetic fields. In other embodiments, the neodymium-containing alloy is used with other implants to attract cells, such as stem cells, or other microorganisms.

In certain embodiments, the biodegradable metal scaffold is made from a magnesium alloy having a magnesium content of at least 96 wt. %, a manganese content from 3.5-4 wt. %, and at least one rare earth metal in an amount from 0.5-3 wt. %.

In other embodiments, the biodegradable metal scaffold is made from a magnesium alloy having a magnesium content of 96-97.9 wt. %, a manganese content of 1.6-2 wt. %, and a rare earth metal content of 0.5-2 wt. %.

In some embodiments, the biodegradable metal scaffold is made from a magnesium alloy having a magnesium content of 96-97.9 wt. %, a manganese content of 1.6-2 wt. %, and a neodymium or cerium content of 0.5-2 wt. %. In some further embodiments, the neodymium or cerium content is between about 0.5-1.25 wt. %, 0.5-1 wt. %, 0.6-0.9 wt. % or about 0.75 wt. %.

In particular embodiments, the biodegradable metal scaffold is made from a magnesium alloy having a magnesium content of 97.45 wt. %, a manganese content of 1.8 wt. %, and a neodymium or cerium content of 0.75 wt. %.

In some embodiments, the biodegradable metal scaffold has a magnesium content that is less than 60% w/w of the in vivo supporting device. In other embodiments, the biodegradable metal scaffold has a magnesium content that is less than about 58, 56, 54, or 52% w/w of the in vivo supporting device. In still other embodiments, the biodegradable metal scaffold has a magnesium content that is less than 50 w/w of the in vivo supporting device.

In some embodiments, the biodegradable metal scaffold has a magnesium content that is less than 60% v/v of the in vivo supporting device. In other embodiments, the biodegradable metal scaffold has a magnesium content that is less than about 58, 56, 54, or 52% v/v of the in vivo supporting device. In still other embodiments, the biodegradable metal scaffold has a magnesium content that is less than 50% v/v of the in vivo supporting device.

In some embodiments, the biodegradable metal scaffold has a magnesium content that is less than 60% w/v of the in vivo supporting device. In other embodiments, the biodegradable metal scaffold has a magnesium content that is less than about 58, 56, 54, or 52% w/v of the in vivo supporting device. In still other embodiments, the biodegradable metal scaffold has a magnesium content that is less than 50% w/v of the in vivo supporting device.

The biodegradable metal scaffold can be expandable. In one embodiment, the biodegradable metal scaffold is of two different diametrical dimensions due to radial deformation of its elastic elements. Before being positioned at the place of reconstruction, the biodegradable metal scaffold is deformed/compressed/folded so as to minimize its diametrical dimension. Then the biodegradable metal scaffold is placed, in the deformed state, inside a transporting means by arranging it on a special setting bulb. Once the biodegradable metal scaffold has been transported to the place of reconstruction, the setting bulb is expanded so that the biodegradable metal scaffold diameter is maximized. In another embodiment, the biodegradable metal scaffold has a plurality of flexible or foldable channel walls or leaflets extending from the center rod/hub/cam. The channel walls or leaflets are kept in a folded position during the delivery process and are released only at the treatment site. In other embodiments, the biodegradable metal scaffold is balloon-expandable or is made from a self-expanding metal or alloy, such as nitinol.

FIG. 1 shows an exemplary biodegradable metal scaffold for a stent. In this embodiment, the scaffold 10 comprises a tubular body 12 and thin struts 14. The struts may have a cross-sectional shape substantially in the form of a square, rectangle, trapezoid, circle or oval. A cross-section of the strut may be further defined by its width, diameter or average thickness.

In certain embodiments, the strut 14 may have a width, diameter or average thickness between 10-300 µm, 10-250 µm, 10-200 µm, 10-150 µm, 10-100 µm, 10-80 µm, 10-60 µm, 10-40 µm, 10-20 µm, 40-300 µm, 40-250 µm, 40-200 µm, 40-150 µm, 40-100 µm, 40-80 µm, 40-60 µm, 80-350 µm, 80-300 µm, 80-250 µm, 80-200 µm, 80-150 µm, 80-120 µm, 100-300 µm, 100-250 µm, 100-200 µm, 100-150 µm, 105-135 µm, 110-130 µm, 115-125 µm, 120-350 µm, 120-300 µm, 120-250 µm, 120-200 µm, 120-150 µm, 150-350 µm, 150-300 µm, 150-250 µm, 150-200 µm, and combinations thereof. In particular embodiments, the strut 14 may have a width, diameter or average thickness of about 120 µm.

Exemplary strut cross-sections may be square or rectangular, for example, 120×120 µm, 140×140 µm, 150×150 µm, 160×160 µm, 170×170 µm, 180×180 µm, 190×190 µm, 200×200 µm, and combinations thereof. Exemplary strut cross-sectional areas may range from 10,000-50,000 $\mu m^2$, 10,000-40,000 $\mu m^2$, 10,000-30,000 $\mu m^2$, 10,000-20,000 $\mu m^2$, 15,000-40,000 $\mu m^2$, 15,000-30,000 $\mu m^2$, 15,000-20,000 $\mu m^2$, 20,000-50,000 $\mu m^2$, 20,000-40,000 $\mu m^2$, 20,000-30,000 $\mu m^2$, 20,000-25,000 $\mu m^2$, 30,000-50,000 $\mu m^2$, 30,000-45,000 $\mu m^2$, 30,000-40,000 $\mu m^2$, 40,000-50,000 $\mu m^2$, or combinations thereof. In some embodiments, the strut cross-sectional area is about 14,400 $\mu m^2$.

The struts in the metal scaffold may be arranged according to a defined architecture. In one embodiment, the metal scaffold in the form of a stent. Typically, a stent includes a plurality of struts arranged to form a generally tubular structure that can be expanded or retracted between a plurality of different diameters. In one aspect, the supporting device comprises a bidirectional stent. In one embodiment, the bidirectional stent includes a cylinder-shaped stent body containing a plurality of axially arranged rows of struts encircling a central lumen in which each of row of struts comprises struts inter-connected to form a wave-pattern with alternating peaks and troughs, whereby each peak has a tip and each trough has a bottom. The rows of struts form one or more row sections comprising at least one row of struts and a plurality of non-flex connectors connecting adjacent rows of struts within each row section, each of the plurality of non-flex connectors comprising a first end and a second end, whereby the first end is attached to a tip of a peak in a first row of struts, and the second end is attached to a tip of a peak in a second row of struts, whereby the first and second rows of struts are within the same row section and are adjacent to each other such that no non-flex connector is present in a row section containing only one row of struts. The rows of struts further comprise a plurality of flex connectors connecting adjacent row sections, each of the plurality of flex connectors comprising a first end and a second end, whereby the first end is attached to a bottom of a first trough in an edge row of struts of a first row section, the first trough having a first trough amplitude, whereby the second end is attached to a bottom of a second trough in an edge row of struts of a second row section, and the second trough having a second trough amplitude, whereby the first row section is adjacent to said second row section. As such, the stent body is capable of being twisted clockwise or counter-clockwise from one end of said stent body by one-fourth of a turn, or more, without causing deformation of any struts, non-flex connectors or flex-connectors in the stent body.

In some embodiments each of the flex connectors includes a first arm having a first end, a second arm having the second end, and a middle section connecting the first arm to the second arm, whereby the first arm has a length that is the same as, or longer than said first trough amplitude, the second arm has a length that is the same as, or longer than said second trough amplitude, and the middle section forms a first angle with the first arm and a second angle with the second arm, such that the first angle is in a range of about 90-160 degrees and the second angle is in a range of about 90-160 degrees. In a further embodiment, each of the first and second angles is in a range of about 90-120 degrees.

Exemplary strut designs for use with the supporting devices of the present invention include those described in U.S. Patent Application Publication Nos. 2010/0256729, 2010/0256731, 2011/0301696 and 2015/0209167, the disclosures of which are incorporated by reference herein.

In certain embodiments, the biodegradable metal scaffold with thin struts is made from a magnesium alloy. In one embodiment, the biodegradable metal scaffold with thin struts is made from a magnesium alloy having a magnesium content of at least 96 wt. %, a manganese content of at least 1 wt. %, and at least one metal from the rare earth metal group in the amount of at least 0.5 wt. %. In another embodiment, the biodegradable metal scaffold is made from a magnesium alloy having a magnesium content of 96-97.9 wt. %, a manganese content of 1.6-2 wt. %, and at least one metal from the rare earth metal group in the amount of 0.5-2 wt. %. In some embodiments, the biodegradable metal scaffold is made from a magnesium alloy having a magnesium content of 96-97.9 wt. %, a manganese content of 1.6-2 wt. %, and a neodymium or cerium content of 0.5-2 wt. %. In some further embodiments, the neodymium or cerium content is between about 0.5-1.25 wt. %, 0.5-1 wt. %, 0.6-0.9 wt. % or about 0.75 wt. %. In another embodiment, the biodegradable metal scaffold is made from a magnesium alloy having a magnesium content of 97.45 wt. %, a manganese content of 1.8 wt. %, and a neodymium or cerium content of 0.75 wt. %. Compared to regular magnesium alloys that do not contain manganese, the manganese-containing magnesium alloys have significantly increased mechanical strength and significantly less or slower hydrogen gas production after implantation. In other embodiments, the biodegradable metal scaffold with thin struts is made from magnesium alloys with a high zinc content (e.g., 28 wt % or higher) to reduce hydrogen production after implantation.

In certain embodiments, the biodegradable metal scaffold constitutes less than 70%, less than 65%, less than 60%, less than 55%, less than 50%, less than 45%, less than 40%, less than 35%, less than 30%, less than 25%, less than 20%, less than 15%, or less than 10% by weight (w/w) of the in vivo supporting device, or a percent range between any two of these integer values.

Alternatively, the biodegradable metal scaffold constitutes less than 70%, less than 65%, less than 60%, less than 55%, less than 50%, less than 45%, less than 40%, less than 35%, less than 30%, less than 25%, less than 20%, less than 15%, or less than 10% by weight (v/v) of the in vivo supporting device or a percent range between any two of these integer values.

In certain embodiments, the biodegradable metal scaffold has a magnesium content, iron content, or zinc content that is less than 70%, less than 65%, less than 60%, less than 55%, less than 50%, less than 45%, less than 40%, less than 35%, less than 30%, less than 25%, less than 20%, less than 15%, or less than 10% by weight (w/w) of the in vivo supporting device, or has a percent magnesium range between any two of these integer values (relative to the supporting device).

Alternatively, the biodegradable metal scaffold has a has a magnesium content, iron content, or zinc content that is less than 70%, less than 65%, less than 60%, less than 55%, less than 50%, less than 45%, less than 40%, less than 35%, less than 30%, less than 25%, less than 20%, less than 15%, or less than 10% by weight (v/v) of the in vivo supporting device, or has a percent magnesium/iron/zinc range between any two of these integer values (relative to the supporting device).

In some embodiments, the biodegradable metal scaffold constitutes a minor component of the supporting device or contributes less than 50% of the overall mechanical strength of the supporting device. In certain embodiments, the biodegradable metal scaffold constitutes a minor component of the supporting device and contributes less than 50% of the overall mechanical strength of the supporting device.

In some embodiments, the biodegradable metal scaffold has a yield strength of at least 180 MPa, at least 200 MPa, or at least 220 MPa. In some embodiments, the biodegradable metal scaffold has an ultimate tensile strength of at least 240 MPa, at least 260 MPa, at least 280 MPa, at least 300 MPa, at least 320 MPa, at least 340 MPa, at least 360 MPa, or at least 380 MPa. In some embodiments, the biodegradable metal scaffold has an elongation at break value of at least 10%, at least 12%, at least 14%, at least 16%, at least 18%, at least 20%, or at least 22%.

In some embodiments, the supporting device contains magnesium as a minor component of the supporting device. In some embodiments, the supporting device contains magnesium as a minor component at 10-30 wt % of the total device. In some embodiments, the magnesium constitutes a minor component of the supporting device and contributes to less than 50% of the overall mechanical strength of the supporting device.

In other embodiments, the biodegradable metal scaffold contributes less than 50% of the structural performance of the in vivo supporting device. As used herein, "structural performance" refers to the ability of the in vivo supporting device to maintain its expanded diameter within a body lumen when emplaced and hold the lumen open. For example, when the biodegradable metal scaffold contributes 50% of the structural performance of the device, it means that the scaffold is providing 50% of the force necessary to hold the lumen open, while other components of the device, such as the biodegradable coating, are providing the remaining 50% of the force necessary to hold the lumen open.

Metal alloys may be produced by conventional casting, mechanical alloying, electrodeposition or by fine microstructure oriented processes. To improve the mechanical and corrosion properties of the metal alloy, processing techniques, including severe plastic deformation (SPD), based on Hall-Petch strengthening and homogenous distribution of precipitates, physical or chemical vapor deposition, cold spraying, equal-channel annular pressing (ECAP), accumulative roll bonding (ARB) and compressive torsion processing (CTP) may be employed.

One approach to improve ductility is to reduce the grain size of the metallic structure (refining). Refining includes all metallurgical measures that lead to a small grain size of an alloy. In general, this presupposes increasing the seed count in the melt in solidification or in the solid state by finely dispersed precipitates. Refining has an advantageous effect on the mechanical properties, in particular, the ductility of the alloy. Reducing the grain size in relation to conventional can provide improved ductility. Microstructure oriented processes can produce microstructures in a metal alloy of defined grain sizes and can eliminate low material ductility and metallic scaffold cracking by having lower extrinsic inclusion content.

To achieve such microstructures, the implant or implant sub-component the implant or implant sub-component may be processed from a melt by a process that controls the direction of solidification along its elongated axis. This may be achieved through controlled heat removal (under-cooling) at one end of the elongated structure so that crystal nucleation and propagation is driven down its length (z axis), while crystal formation in the directions perpendicular to elongated axis are retarded by keeping those surfaces at an elevated temperature with insufficient under-cooling for nucleation. Additional mechanical forming processes can be practiced following directional solidification to achieve the final implant geometry, if the thermal treatments do not result in a re-crystallization that reverts the structure to polycrystalline. Processes for forming microstructures, as described in e.g., U.S. Patent Application Publication No. 20150157767, may be employed that are tailored to manifest sufficient ductility in a balloon-expandable stent design, such as a Mg alloy stent, so that the stent can be crimped onto a balloon catheter, wiggled through a long tortuous path, and expanded to fill the diameter of the artery without fracturing.

A microstructure of material can be at least partially dependent on the processing techniques and parameters. The grains (i.e., crystals) of a magnesium alloy can align themselves with their basal planes parallel to the direction of the processing material flow, which can result in different mechanical properties in the direction of flow as compared to the a direction perpendicular to the direction of flow. In the case of extruding stent tubing including the alloys of Table II, the resulting tube may have a strong preferred crystal orientation, aligning the basal planes in the extrusion direction, which produces increased ductility in the extrusion direction of the tubing, but less ductility in a direction perpendicular to the extrusion direction. The expansion of a stent, however, relies upon the material having suitable ductility in all directions. A strong grain texture with an unfavorable loading along the c-crystal axis components of the grains causes twinning and void nucleation under lower strains. The twinning with void nucleation can be the initiation of an eventual material failure. Stent tube extrusion may also produce a randomized crystal structure with no preferred orientation, which produces more isotropic mechanical properties, but still suffers from the ductility issues discussed above.

Microstructures can provide superior ductility and other mechanical properties in multiple directions, whereby grain boundaries are decorated with precipitates and/or ceramic nanoparticles. Microstructures provided herein can be characterized in a number of ways. In some embodiments, the microstructures provided herein, when viewed at a 500× using x-ray diffraction, have no more than 3% by area filled with intermetallic ("IM") particles. In some embodiments, the microstructures herein have no more than 2% by area filled with IM particles. In certain embodiments, the maximum IM particle dimension is 30 µm or less, 20 µm or less, 10 µm or less, 5 µm or less, or 1 µm or less.

In some embodiments, the grain boundaries can be decorated with ceramic nanoparticles. Ceramic nanoparticles can pinch grain boundaries and/or impede grain growth during processing of the material, which can result in a fine grain microstructure of the magnesium alloy. The fine grain microstructure of a magnesium alloy can increase strength and ductility of the material. In one embodiment, the microstructures have at least 0.5% by area filled with ceramic particles, at least 1.0% by area filled with ceramic particles, between 0.5% and 5% by area filled with ceramic particles, between 1.0% and 3% by area filled with ceramic particles, or about 1.5% by area filled with ceramic particles.

Ceramic nanoparticles provided in a composite can have any appropriate dimensions. In some embodiments, ceramic nanoparticles used in a composite provided herein have an average largest diameter of between 0.5 nm and 500 nm, between 1.0 nm and 200 nm, between 5 nm and 100 nm, between 10 nm and 100 nm, between 25 nm and 75 nm, or between 40 nm and 60 nm. In some embodiments, a maximum ceramic nanoparticle dimension will be 5 μm or less. In some embodiments, a maximum ceramic nanoparticle dimension will be 1 μm or less, 500 nm or less, 5 μm or less, or 200 nm or less.

Ceramic nanoparticles in a composite can include any suitable ceramic material. In some embodiments, the ceramic nanoparticles are insoluble in the metal alloy used in a composite provided herein. In some embodiments, the ceramic nanoparticles include one or more of the following ceramic materials: TiC, $TiO_2$ $Si_3N_4$, AlN, $Al_2O_3$, $CeO_2$, Boron Nitride, $B_4C$, and $Y_2O_3$. In other embodiments, the ceramic nanoparticles in the composite include a radiopaque ceramic material. In some embodiments, the ceramic nanoparticles in the composite have an electro-motive force within 50%, within 25%, within 10% or within 5% of the electro-motive force of magnesium. Suitable ceramic nanoparticles are available from SkySpring Nanomaterials, Houston Tex.

The microstructures provided herein can include equiaxed Mg-rich solid solution-phase grains with second-phase precipitates and/or ceramic nanoparticles located within smooth and equiaxed alpha-phase-grain boundaries. In some embodiments, the equiaxed equiaxed Mg-rich solid solution-phase grains have an average grain size of 20 μm or less, 15 μm or less, 10 μm or less, 7.5 μm or less, 5 μm or less, 4 μm or less, 3 μm or less, 2 μm or less, or 1 μm or less. In other embodiments, the equiaxed Mg-rich solid solution-phase grains have an average grain size of between 0.1 μm and 10 μm, of between 0.5 μm and 5 μm, or between 1 μm and 4 μm. In some embodiments, at least 90% by volume of the secondary phase particles can be found along alpha phase grain boundaries. In some embodiments, the average secondary phase individual particle diameter or longest dimension is 1 μm or less, 500 nm or less, 300 nm or less, 200 nm or less, 100 nm or less, 75 nm or less, 50 nm or less, or 25 nm or less. In some embodiments, the average secondary phase individual particle diameter or longest dimension is between 0.1 nm and 1 μm, between 0.5 nm and 500 nm, between 5 nm and 300 nm, between 10 nm and 200 nm, between 20 nm and 100 nm, between 25 nm and 75 nm, or between 40 nm and 60 nm. The microstructure provided herein can have a reduced number of twin bands. In some embodiments, less than 15% of the alpha grains will have twin bands. In other embodiments, the number of alpha grains having twin bands can be less than 10%, less than 5%, or less than 1% when the stent is cut and crimped.

The inclusion of these microstructures can overcome the basal plane alignment by randomizing grain orientations, resulting in isotropic mechanical properties. Finer grains can also yield increased grain boundary areas, which can provide more grain boundary slip. Refinement of precipitate diameters may also allow additional grain boundary slip. Moreover, a homogenous dispersion of secondary-phase precipitates and/or ceramic nanoparticles along the grain boundaries can improve strength and corrosion resistance. In some embodiments, the precipitates and/or ceramic nanoparticles can be substantially centered on the grain boundary but be larger than the width of the grain boundary.

In certain embodiments, the microstructures can be formed by using the following process steps: (a) mix elements to form a molten metal alloy, such as a magnesium alloy (and optionally add ceramic nanoparticles); (b) cooling the molten metal alloy to form a ingot or billet; (c) solution treating a billet to solutionize any intermetallic precipitates formed during solidification of the alloy; (d) controlled cooling after solutionizing to form a distribution of fine discontinuous or continuous precipitates along grain boundaries; and (e) thermomechanical deformation of the material after or during cooling to refine the metal rich solid solution (e.g., Mg-rich) grain size and produce a substantially equiaxed grain morphology.

For example, an ingot or billet can be formed or machined into a solid or hollow rod, homogenized, subjected to a high-strain process to refine the microstructure, and then shaped or machined into stent tubing from which the stent is manufactured into final dimensions (e.g., the dimensions of a stent body). In some cases, the billet or ingot can be formed into an endoprosthesis that does not normally undergo expansion, for example vascular closing plugs or embolical material (e.g., microbeads used to close off unwanted vascular structures or cancerous tissue).

Billets can be made using any suitable process. A billet can have a diameter of between 2 centimeters and 1 meter. In some cases, an ingot of a desired biodegradable magnesium alloy can be made by conventional melting and solidification in a mold (liquid casting), thixomolding (semi-solid processing) or powder metallurgy (solid-processing). The ingot can then be machined to the desired dimensions of the billet which will serve as the feedstock for subsequent processing and shaping. In some cases, a billet can be formed without additional machining process. To form an endoprosthesis (e.g., a stent body) out of a billet, the billet can be converted into a rod or hollow tube having a smaller diameter. In some cases, the ingot or billet is converted into a rod or hollow tube after the ingot or billet is homogenized. In some cases, the rod or hollow tube can have an outer diameter of between 1 centimeter and 6 centimeters. In the case of a stent, a hollow tube provided herein can then be further reduced in diameter and cut to form individual stent bodies, including fenestrations between stent struts. In some cases, the stent struts can have a width to thickness ratio of less than 1.2. In some cases, the thickness of the hollow tube and the stent struts can be between 80 μm and 160 μm.

An ingot or billet, in some cases, can be made by thixomolding the elements of the biodegradable magnesium alloy (and optionally ceramic nanoparticles). Thixomolding involves mixing solid constituents into a portion of the composition that is in a liquid phase and then cooling the mixture to reach a fully solid state. Thixomolding can reduce the number and size of brittle inter-metallic (IM) particles in the alloy. For example, thixomolding can use a machine similar to an injection mold. Room temperature magnesium alloy chips, chips of the other alloy constituents, and optionally ceramic nanoparticles can be fed into a heated barrel through a volumetric feeder. The heated barrel can be filled with an inert gas (e.g., argon) to prevent oxidation of the magnesium chips. A screw feeder located inside the barrel can feed the magnesium chips and other alloy constituents forward as they are heated into a semi-solid temperature range. For example, the mixture can be heated to a temperature of about 442° C. The screw rotation can provide a shearing force that can further reduce the size of IM particles. Once enough slurry has accumulated, the screw can move forward to inject the slurry into a steel die having the shape of an ingot or billet.

An ingot or billet, in some cases, can be made by combining the elements of the biodegradable magnesium alloy using powder metallurgy. Powder metallurgy involves the solid-state sintering of elemental or pre-alloyed powder particles and optionally ceramic nanoparticles. Using fine powders in a sintering process can avoid the formation of coarse IM particles. For example, fine powders of magnesium, other alloying constituents, and optionally ceramic nanoparticles can be blended into a homogenous mixture, pressed into a desired shape (e.g., the shape of the ingot or billet), and heated while compressed to bond the powders together. Sintering can be conducted in an inert atmosphere (e.g., argon) to avoid oxidation of the magnesium.

An ingot or billet including all of the desired elements of a biodegradable magnesium alloy and the optional ceramic nanoparticles can be homogenized to reduce elemental concentration gradients. The ingot or billet can be homogenized by heating the ingot or billet to an elevated temperature below the liquidus temperature of the biodegradable magnesium alloy and holding the ingot or billet at that temperature for period of time sufficient to allow elemental diffusion within the ingot or billet to reduce elemental concentration gradients within the ingot or billet.

Homogenizing the ingot or billet can solutionize intermetallic (IM) second-phase precipitate particles, because the homogenization temperature is in excess of the phase boundary (solvus temperature) between the high-temperature single, solid phase (alpha) and two-phase field boundary on the Mg—Al phase diagram. A follow-on solutioning treatment at the same or similar position within the phase diagram can be used in some cases to refine the precipitate structure. For example, a follow-on solutioning treatment can be used if the homogenization treatment cooling was not controlled sufficiently to tailor the second-phase precipitate size and location. In some cases, the ingot or billet is cooled rapidly after holding the ingot or billet at the elevated temperature in order to form relatively fine IM second-phase precipitates. For example, the ingot or billet can be cooled from the elevated hold temperature via force gas cooling or liquid quenching. The ingot or billet can be homogenized in an inert atmosphere (e.g., in an argon atmosphere) or open atmosphere so long as surface oxides are removed. In some cases, the ingot or billet provided herein can be homogenized at a temperature of between 400° C. and 450° C. In some cases, the ingot or billet is held at a temperature of between 400° C. and 450° C. for at least 2 hours, at least 3 hours, or at least 4 hours. In some cases, the hold time at an elevated temperature is between 4 hours and 24 hours. For example, a biodegradable magnesium alloy ingot having a diameter of about 15 centimeters can be heated to a temperature of 440° C. for 6 hours to homogenize the ingot, followed by quenching the ingot in a cooled argon gas stream.

An ingot or billet can be subjected to one or more high-strain processes to refine the microstructure into a microstructure provided herein. In some cases, the high-strain processes can include one or more equal-channel high-strain processes. Equal-channel high-strain processes include Equal-Channel Angular Extrusion ("ECAE") and Equal-Channel Angular Pressing ("ECAP"). ECAE is an extrusion process that produces significant deformation strain without reducing the cross sectional area of the piece. ECAE can be accomplished by extruding the alloy (e.g., a billet of the alloy) around a corner. For example, a billet of a biodegradable magnesium alloy can be forced through a channel having a 90 degree angle. The cross section of the channel can be equal on entry and exit. The complex deformation of the metal as it flows around the corner can produce very high strains. In some cases, an ingot can be machined into a billet having the exact dimensions of the channel of an ECAE die prior to an ECAE process. Because the cross section can remain the same, the billet can be extruded multiple times with each pass introducing additional strain. With each ECAE process, the orientation of the billet can be changed to introduce strain along different planes. In some cases, an ECAE die can include multiple bends.

The Biodegradable Polymer Coating

The biodegradable polymer coating comprises one or more biodegradable polymers. The biodegradable polymer coating may coat the abluminal side of the metal scaffold, the luminal side of the metal scaffold, or both. In some embodiments, the biodegradable coating coats all sides of the struts of the metal scaffold. The biodegradable polymer coating may comprises a single polymer layer or it may comprise a multilayer coating.

Examples of biodegradable polymers include, but are not limited to, polylactides, copolymers of D- and L-lactides, polyglycolides, copolymers of the polylactides and polyglycolides, including poly (D, L-lactide/glycolide) copolymers, polylactic acid (PLLA), polylactic-co-glycolic acid (PLGA), polydioxanone, polycaprolactone, polygluconate, poly(lactic acid) polyethylene oxide copolymer, modified cellulose, polyhydroxybutyrate, polyamino acids, polyphosphate ester, polyvalerolactone, poly-ε-decalactone, polylactonic acid, polyglycolic acid, poly-ε-caprolactone, polyhydroxybutyric acid, polyhydroxybutyrates, polyhydroxyvalerates, polyhydroxybutyrate-co-valerate, poly(1,4-dioxane-2,3-one), poly (1,3-dioxane-2-one), poly-para-dioxanone, polyanhydrides, polymaleic acid anhydrides, polyhydroxy methacrylates, fibrin, polycyanoacrylate, polycaprolactone dimethylacrylates, poly-β-maleic acid, polycaprolactone butyl acrylates, multiblock polymers from oligocaprolactonediols and oligodioxanonediols, polyether ester multiblock polymers from PEG and poly(butylene terephthalates), polypivotolactones, polyglycolic acid trimethyl carbonates, polycaprolactone glycolides, poly(γ-ethyl glutamate), poly(DTH-iminocarbonate), poly(DTE-co-DT-carbonate), poly(bisphenol A-iminocarbonate), polyorthoesters, polyglycolic acid trimethyl carbonate, polytrimethyl carbonates, polyiminocarbonates, poly(N-vinyl)-pyrrolidone, polyvinyl alcohols, polyester amides, glycolized polyesters, polyphosphoesters, polyphosphazenes, poly[p-carboxyphenoxy)propane], polyhydroxy pentanoic acid, polyanhydrides, polyethylene oxide propylene oxide, soft polyurethanes, polyurethanes having amino acid residues in the backbone, polyetheresters such as polyethylene oxide, polyalkene oxalates, polyorthoesters as well as copolymers thereof, lipids, carrageenans, fibrinogen, starch, collagen, protein based polymers, polyamino acids, synthetic polyamino acids, zein, polyhydroxyalkanoates, pectic acid, actinic acid, carboxymethyl sulfate, albumin, hyaluronic acid, chitosan and derivatives thereof, heparan sulfates and derivates thereof, heparins, chondroitin sulfate, dextran, β-cyclodextrins, copolymers with PEG and polypropylene glycol, gum arabic, guar, gelatin, collagen N-hydroxysuccinimide, lipids, phospholipids, polyacrylic acid, polyacrylates, polymethyl methacrylate, polybutyl methacrylate, polyacrylamide, polyacrylonitriles, polyamides, polyetheramides, polyethylene amine, polyimides, polycarbonates, polycarbourethanes, polyvinyl ketones, polyvinyl halogenides, polyvinylidene halogenides, polyvinyl ethers, polyisobutylenes, polyvinyl aromatics, polyvinyl esters, polyvinyl pyrrolidones, polyoxymethylenes, polytetramethylene oxide, polyethylene, polypropylene, polytetrafluoroethylene, polyurethanes, polyether urethanes, silicone polyether urethanes, silicone polyurethanes, silicone polycarbonate urethanes, polyolefin elastomers, EPDM gums, fluorosilicones, carboxymethyl chitosans polyaryletheretherketones, polyetheretherketones, polyethylene terephthalate, polyvalerates, carboxymethylcellulose, cellulose, rayon, rayon triacetates, cellulose nitrates, cellulose acetates, hydroxyethyl cellulose, cellulose butyrates, cellulose acetate butyrates, ethyl vinyl acetate copolymers, polysulfones, epoxy resins, ABS resins, silicones such as polysiloxanes, polydimethylsiloxanes, polyvinyl halogens and copolymers, cellulose ethers, cellulose triacetates, chitosans and copolymers and/or mixtures of the aforementioned polymers. In particular embodiments, the biodegradable polymer comprises PLLA, PLGA or a combination thereof. In some further embodiments, the biodegradable polymer consists essentially of PLLA, PLGA or a combination thereof. In still further embodiments, the biodegradable polymer consists of PLLA, PLGA or a combination thereof.

In some embodiments, the biodegradable polymer coating has a substantially uniform thickness ranging from 10 μm-200 μm (i.e., the coating/covering has the same thickness throughout the coated/covered area. In other embodiments, the biodegradable polymer coating has a thickness varying within the range of 10 μm-200 μm (i.e., the coating/covering has different thicknesses in different areas).

In some embodiments, the polymer coating has a thickness between 10-200 μm, 10-150 μm, 10-100 μm, 10-80 μm, 10-50 μm, 10-30 μm, 10-25 μm, 15-25 μm, 12-24 μm, 20-200 μm, 20-150 μm, 20-100 μm, 20-80 μm, 20-50 μm, 40-200 μm, 40-150 μm, 40-100 μm, 40-60-200 μm, 60-150 μm, 60-120 μm, 60-90 μm, 80-200 μm, 80-150 μm, 80-120 μm, 80-100 μm, 100-200 μm, 100-150 μm, 100-120 μm, 120-200 μm, 120-150 μm, 150-200 μm, and combinations thereof, including integers thereof. In some embodiments, the polymer coating has a thickness of 20 μm or about 20 μm.

To modify the degradation profile of the polymer coating, polymers of different molecular weights may be used. For example, in some embodiments, the polymer has an average molecular weight of less than less than 1 kDa, less than 5 kDa, less than 10 kDa, less than 15 kDa, less than 20 kDa, less than 25 kDa, less than 30 kDa, less than 40 kDa, less than 50 kDa, less than 75 kDa, less than 100 kDa, less than 150 kDa, less than 200 kDa, less than 250 kDa, less than 300 kDa, less than 400 kDa, less than 500 kDa, or a range between any two of these integer values.

In certain embodiments where thin metal struts are employed, the biodegradable polymer coating can provide additional strength to the structural performance of the device for supporting a lumen or vessel. In some embodiments, the biodegradable metal scaffold is expandable after implantation to an expanded form having different diameters at each end of the scaffold, whereby the polymer coating helps the scaffold to maintain these diameters after implantation.

In certain embodiments, the polymeric coating layer or multilayer polymeric coating has an elastic modulus between 300-3000 MPa, between 500 to 2500 Mpa, or between 800-1600 Mpa with a percent elongation of between 10% to 300% at failure.

The struts may be partially covered or fully covered. The struts may be covered on the abluminal side, luminal side, or both. In some embodiments, the biodegradable polymer coating coats metal struts of the biodegradable metal scaffold but does not cover openings between struts. In other embodiments, the biodegradable polymer coating coats metal struts of the biodegradable metal scaffold and covers openings between struts. In other embodiments, the biodegradable polymer coating coats metal struts of the biodegradable metal scaffold but does not cover openings between struts. In yet other embodiments, the biodegradable polymer coating covers the coated metal struts and openings between the metal struts. In some embodiments, the struts are fully covered with a biodegradable polymer coating layer.

In some embodiments of the in vivo supporting device, the supporting structure struts have a thickness from the luminal side to the abluminal side of the device of between about 20 μm and about 250 μm. In certain embodiments, the supporting structure struts have a thickness from the luminal side to the abluminal side of the device of about 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, or 250 μm. In some embodiments, the thickness from the luminal side to the abluminal side is a cross-sectional thickness. In other embodiments, the thickness from the luminal side to the abluminal side is a maximal thickness.

In some embodiments of the in vivo supporting device, the biodegradable coating has a thickness on one side, each side, multiple sides or surrounding a strut of the supporting structure of between about 5 μm and about 100 μm. In certain embodiments, the biodegradable coating has a thickness of about 5, 10, 15, 18, 20, 22, 25, 30, 35, 40, 45, 50, 55, 60, 65, 70, 75, 80, 85, 90, 95, or 100 μm. In some embodiments, the biodegradable coating is applied only to the luminal surface of the supporting structure struts. In other embodiments, the biodegradable coating is applied only to the abluminal surface of the supporting structure struts. In still other embodiments, the biodegradable coating is applied only to the luminal and abluminal surfaces of the supporting structure struts, but not between the struts. In still other embodiments, the biodegradable coating is applied only to the luminal and abluminal surfaces of the supporting structure struts, but not between the struts. In yet other embodiments, the biodegradable coating is applied completely surrounding the struts.

In some embodiments, the supporting structure struts have a thickness of between about 90 and 150 μm and the biodegradable coating has a thickness on one side, each side, multiple sides or surrounding a strut of the supporting structure of between about 5 μm and about 35 μm. In other embodiments, the supporting structure struts have a thickness of between about 100 μm and 140 μm and the biodegradable coating has a thickness on one side, each side, multiple sides or surrounding a strut of the supporting structure of between about 10 μm and about 30 μm. In still other embodiments, the supporting structure struts have a thickness of between about 110 μm and 130 μm and the biodegradable coating has a thickness on one side, each side, multiple sides or surrounding a strut of the supporting structure of between about 15 μm and about 25 μm. In yet other embodiments, the supporting structure struts have a thickness of between about 115 μm and 125 μm and the biodegradable coating has a thickness on one side, each side, multiple sides or surrounding a strut of the supporting structure of between about 18 µm and about 22 µm. In some related embodiments, the biodegradable metal scaffold is made from a magnesium alloy having a magnesium content of 96-97.9 wt. %, a manganese content of 1.6-2 wt. %, and a neodymium or cerium content of 0.5-2 wt. %. In some further related embodiments, the neodymium or cerium content is between about 0.5-1.25 wt. %, 0.5-1 wt. %, 0.6-0.9 wt. % or about 0.75 wt. %. In another related embodiment, the biodegradable metal scaffold is made from a magnesium alloy having a magnesium content of 97.45 wt. %, a manganese content of 1.8 wt. %, and a neodymium or cerium content of 0.75 wt. %. In particular related embodiments, the biodegradable polymer comprises PLLA, PLGA or a combination thereof. In some further related embodiments, the biodegradable polymer consists essentially of PLLA, PLGA or a combination thereof. In still further related embodiments, the biodegradable polymer consists of PLLA, PLGA or a combination thereof. In related embodiments, the cross-sectional shape of the strut may be square or rectangular, square or rectangular with rounded corners, generally rounded, circular, oval or elliptical.

In some embodiments, the supporting structure struts have a thickness of between about 90 and 150 µm and the biodegradable coating has a thickness on one side, each side, multiple sides or surrounding a strut of the supporting structure of between about 5 µm and about 35 µm. In other embodiments, the supporting structure struts have a thickness of between about 100 µm and 140 µm and the biodegradable coating has a thickness on one side, each side, multiple sides or surrounding a strut of the supporting structure of between about 10 µm and about 30 µm. In still other embodiments, the supporting structure struts have a thickness of between about 110 µm and 130 µm and the biodegradable coating has a thickness on one side, each side, multiple sides or surrounding a strut of the supporting structure of between about 15 µm and about 25 µm. In yet other embodiments, the supporting structure struts have a thickness of between about 115 µm and 125 µm and the biodegradable coating has a thickness on one side, each side, multiple sides or surrounding a strut of the supporting structure of between about 18 µm and about 22 µm. In some related embodiments, the biodegradable metal scaffold is made from a magnesium alloy having a magnesium content of 96-97.9 wt. %, a manganese content of 1.6-2 wt. %, and a neodymium or cerium content of 0.5-2 wt. %. In some further related embodiments, the neodymium or cerium content is between about 0.5-1.25 wt. %, 0.5-1 wt. %, 0.6-0.9 wt. % or about 0.75 wt. %. In another related embodiment, the biodegradable metal scaffold is made from a magnesium alloy having a magnesium content of 97.45 wt. %, a manganese content of 1.8 wt. %, and a neodymium or cerium content of 0.75 wt. %. In particular related embodiments, the biodegradable polymer comprises PLLA, PLGA or a combination thereof. In some further related embodiments, the biodegradable polymer consists essentially of PLLA, PLGA or a combination thereof. In still further related embodiments, the biodegradable polymer consists of PLLA, PLGA or a combination thereof. In related embodiments, the cross-sectional shape of the strut may be square or rectangular, square or rectangular with rounded corners, generally rounded, circular, oval or elliptical.

In some embodiments, the metal alloy scaffold has a magnesium content of 96-97.9 wt. %, a manganese content of 1.6-2 wt. %, and a neodymium or cerium content of 0.5-2 wt. %., and has a strut thickness of 80-140 µm from the luminal to the transluminal side; the biodegradable coating comprises PLLA, PLGA or a combination thereof, has a thickness of 10-40 µm and is applied only to the luminal side of the strut, resulting in an overall scaffold thickness of 90-180 µm. In some embodiments, the metal alloy scaffold has a magnesium content of 96-97.9 wt. %, a manganese content of 1.6-2 wt. %, and a neodymium or cerium content of 0.75 wt. %., and has a strut thickness of 90-130 µm from the luminal to the transluminal side; the biodegradable coating comprises PLLA, PLGA or a combination thereof, has a thickness of 10-30 µm and is applied only to the luminal side of the strut, resulting in an overall scaffold thickness of 100-160 µm. In some embodiments, the metal alloy scaffold has a magnesium content of 96-97.9 wt. %, a manganese content of 1.6-2 wt. %, and a neodymium or cerium content of 0.75 wt. %., and has a strut thickness of about 120 µm from the luminal to the transluminal side; the biodegradable coating comprises PLLA, PLGA or a combination thereof, has a thickness of about 20 µm and is applied only to the luminal side of the strut, resulting in an overall scaffold thickness of about 140 µm. In some related embodiments, the metal alloy has a magnesium content of 97.45 wt. %, a manganese content of 1.8 wt. %, and a neodymium or cerium content of 0.75 wt. %, and the biodegradable coating consists of PLLA.

In some embodiments, the device contains an additional coating that delays the degradation time of the device or of the metal alloy scaffold of the device. In some embodiments, the coating is on the luminal surface of the device. In other embodiments, the coating is on the abluminal surface of the device. In still other embodiments, the coating is between the metal alloy scaffold and the biodegradable coating.

In some embodiments, the additional coating that delays the degradation time of the device or of the metal alloy scaffold of the device is a coating of iron or other material. In other embodiments, the additional coating is a nano-coating of iron between the metal alloy scaffold and the biodegradable coating.

Figure 2A:
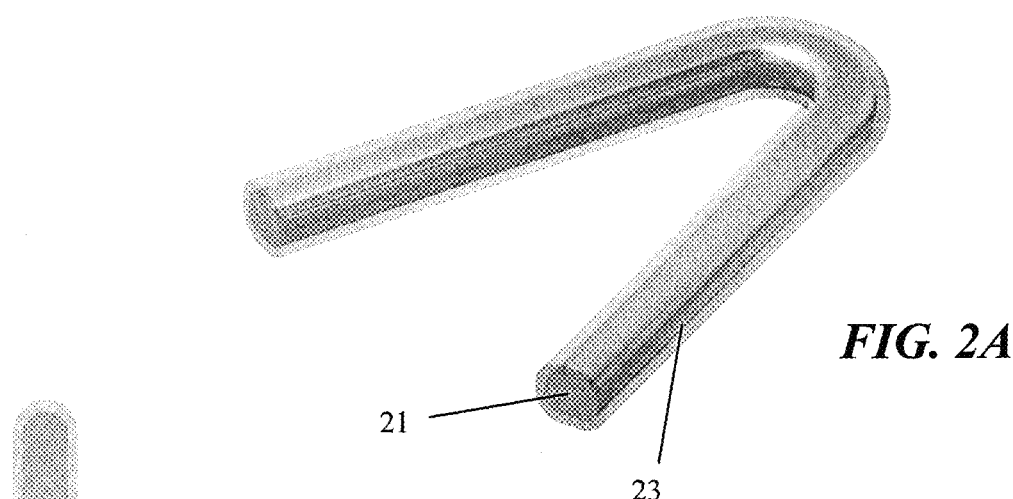
FIGS. 2A-2B show the perspective view (FIG. 2A) and cross sectional view (FIG. 2B) of a stent strut fully covered with a biodegradable polymer coating.
Figure 2B:
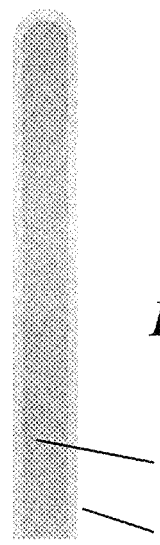

FIGS. 2A-2B show a perspective view (FIG. 2A) and a cross sectional view (FIG. 2B) of a strut 14 having a metal core 21 fully covered with a biodegradable polymer coating 23. This coating is different from the coating used in perforation management devices. The coating 23 can be of varying thickness. In certain embodiments, the metal core 21 starts to degrade after the complete degradation of the polymer coating 23. In other embodiments, the metal core 21 starts to degrade before the polymer coating 23.

In certain embodiments, the biodegradable polymer coating 23 is a porous coating so as to allow some or all of the inner metal core 21 to degrade before the complete degradation of the coating 23. In other embodiments, the biodegradable polymer coating layer 23 has one or more small holes in the coating so as to allow degradation of some or all of the inner core 21 before the complete degradation of the coating 23.

Figure 3A:
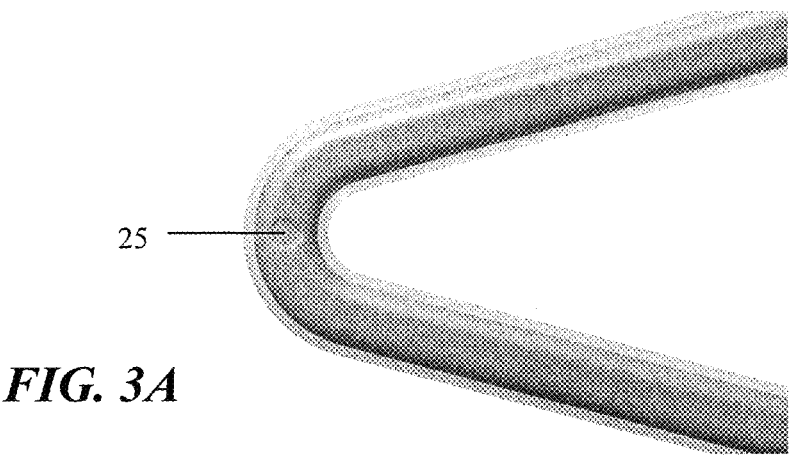
FIGS. 3A-3B show the perspective top view (3A) and cross sectional view (3B) views of a stent strut with a biodegradable core covered with a biodegradable layer and a small opening on the cover.
Figure 3B:
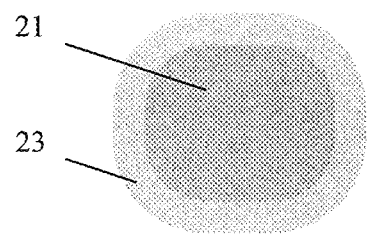

FIGS. 3A-3B show a perspective top view (3A) and a cross sectional view (3B) of a stent strut 14 with a biodegradable core 21 covered with a biodegradable polymer coating 23 and a small opening 25 on the coating 23. The opening 25 allows for direct contact of the inner core 21 with the body fluid and earlier degradation of the core 21.

Figure 4A:
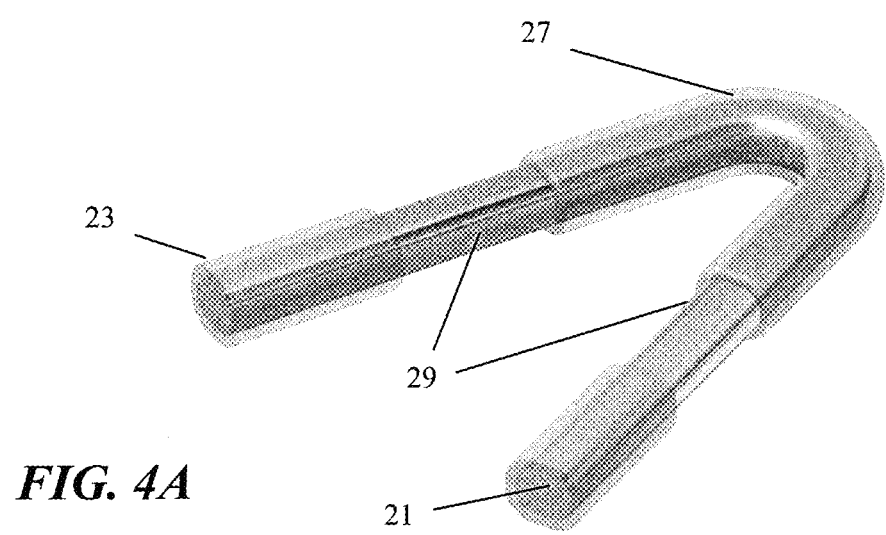
FIGS. 4A-4C show embodiments of stent struts partially covered with a biodegradable layer.
Figure 4B:
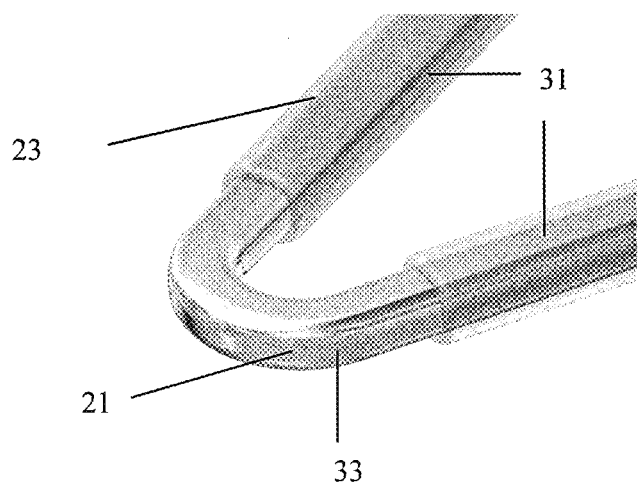
Figure 4C:
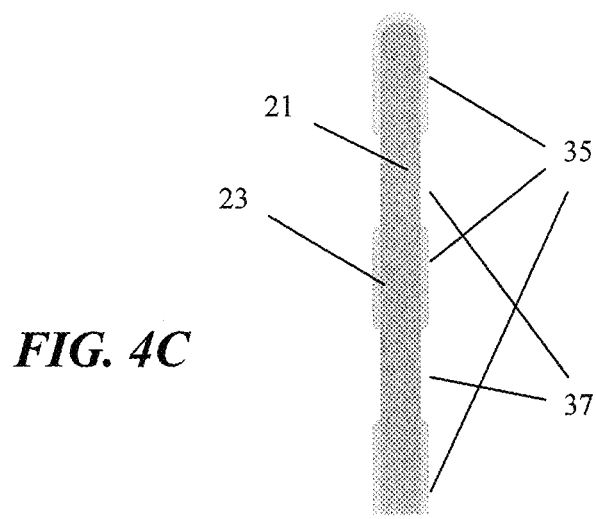

In some embodiments, the strut 14 comprises a metal core 21 partially covered with a biodegradable polymer coating 23. FIGS. 4A-4C show embodiments of a strut 14 having a metal core 21 with one or more covered sections and one or more exposed sections. In one embodiment, the metal core 21 has covered section 27, and an exposed middle section 29 (FIG. 4A). In another embodiment, the metal core 21 has covered sections 31 and an exposed end section 33 (FIG. 4B). In another embodiment, the metal core 21 has multiple covered sections 35 and multiple exposed sections 37 (FIG. 4C) that allow earlier degradation of the device.

In some other embodiments, the metal core 21 is covered with the biodegradable polymer coating 23 on certain sides and surfaces. In one embodiment, the metal core 21 is covered with the biodegradable polymer coating 23 in such a manner that, when placed in a body lumen, the metal core surfaces that face the lumen opening and are exposed to the body fluid in the lumen are covered with the biodegradable polymer coating 23 to reduce the rate of degradation, while the metal core surfaces that are in contact with the lumen wall are not covered.

Figure 5A:
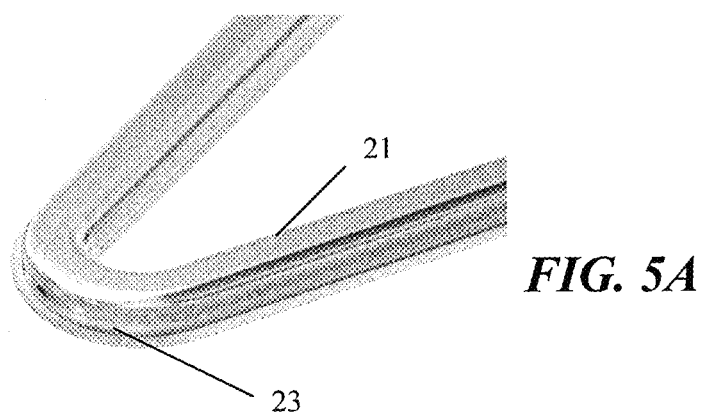
FIGS. 5A-5F show embodiments of stent strut partially covered with a biodegradable layer.
Figure 5B:
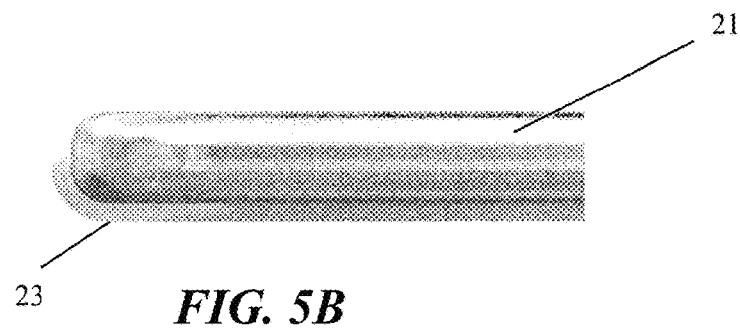
Figure 5C:
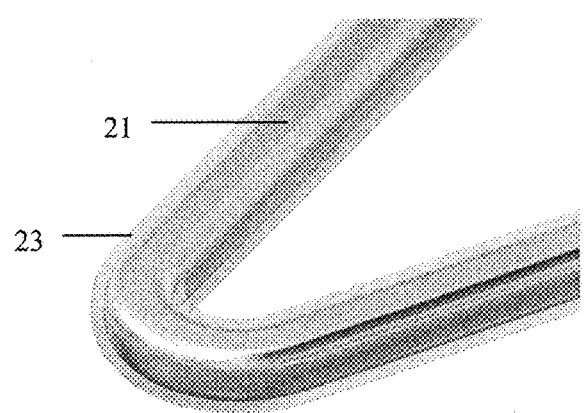
Figure 5D:
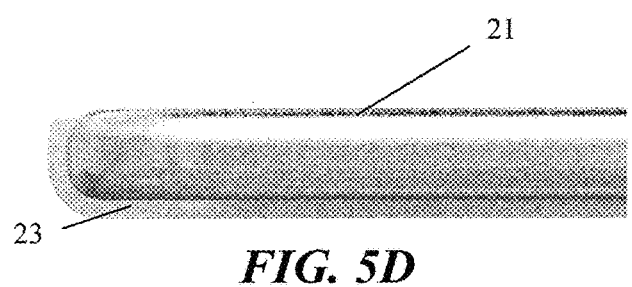
Figure 5F:
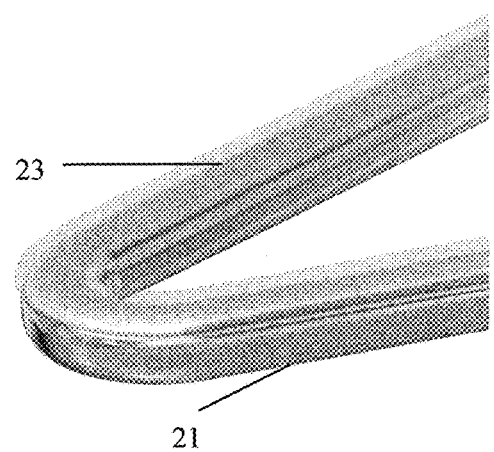
Figure 5E:
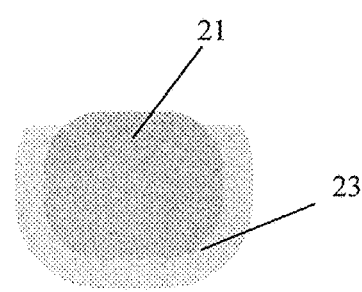

FIGS. 5A-5E show various embodiments of a strut 14 with a side-coated metal core 21. FIGS. 5A and 5B show a perspective view (FIG. 5A) and a cross sectional view (FIG. 5B) of a strut 14 with a coating 23 covering about half of the strut outer surface. FIGS. 5C-5D show a perspective view (FIG. 5C) and cross sectional views (FIGS. 5D, 5Ed 5E) of a strut 14 with a coating 23 that cover more than half of the outer surface of the core 21. FIG. 5F, on the other hand, shows a perspective view of a strut 14 with a coating 23 covering less than half of the strut outer surface.

In certain embodiments, the cross-sectional width of the coated strut has a width between 100-600 µm. The cross-sectional width of the coated strut may range between 120-500 µm, 150-400 µm, 150-300 µm, 150-250 µm, 150-200 µm, 200-500 µm, 200-400 µm, 200-300 µm, 250-500 µm, 250-500 µm, 250-400 µm, 250-300 µm, 300-500 µm, 300-400 µm, 300-350 µm, and combinations thereof.

In certain embodiments, the cross sectional width of the strut is between 80-160 µm and the polymeric coating has a thickness between 5-50 µm. In other embodiments, the cross sectional width of the strut is between 100-140 µm and the polymeric coating has a thickness between 10-40 µm. In one embodiment, the cross sectional width of the strut is about 120 µm and the polymeric coating has a thickness of about 20 µm.

In other embodiments, the cross sectional width of the strut is between 80-250 µm and the polymeric coating has a thickness between 40-120 µm. In certain embodiments, the cross sectional width of the strut is between 125-180 µm and the polymeric coating has a thickness between 60-100 µm. In one embodiment, the cross sectional width of the strut is about 75 µm and the polymeric coating has a thickness of about 75 µm.

In other embodiments, the cross sectional width of the strut is between 120-300 µm and the polymeric coating has a thickness between 50-150 µm. In certain embodiments, the cross sectional width of the strut is between 150-220 µm and the polymeric coating has a thickness between 75-125 µm. In one embodiment, the cross sectional width of the strut is about 180 µm and the polymeric coating has a thickness of about 90 µm.

In some embodiments, the biodegradable polymer coating comprises materials, such as metal particles, that assist with the illumination of the in vivo supporting device under fluoroscopy. Such materials could also be used to help support the material structure of the polymer. In some embodiments, the biodegradable polymer coating comprises polymer material mixed with iron or magnesium nanoparticles to help the polymer material.

In one embodiment, the biodegradable polymer coating comprises a bioabsorbable material that is degraded based on varying levels of pH. For example, the material may be stable at a neutral pH but degrades at a high pH. Examples of such materials include, but are not limited to chitin and chitosan. In another embodiment, the bioabsorbable material is selected based on its sensitivity to degradation by enzymes, such as lysozyme. In another embodiment, the biodegradable polymer coating binds to hydrogen atoms in the body fluid, thereby lowering the local pH to delay degradation and absorption of the biodegradable polymer coating (which is otherwise degraded at higher pH).

In another embodiment, the biodegradable polymer coating comprises a bioabsorbable material that absorbs moisture and expands in situ at the treatment site. For example, a coating made of chitin or a variable copolymer of chitin and PLGA, or chitin and magnesium and other raw earth minerals can swell in volume when contacted with body fluids in vivo. In one embodiment, the in vivo supporting device has a pre-implantation diameter $D_{pre}$ (i.e., dry diameter) and is expandable to a post-implantation diameter $D_{post}$ (i.e., wet diameter) after exposure to body liquid in a lumen. As used hereinafter, the "pre-implantation diameter $D_{pre}$" refers to the largest diameter of a device body before implantation and the "post-implantation diameter $D_{post}$" refers to the largest diameter of the device body after implantation.

In certain embodiments, the biodegradable polymer coating is formulated to have a degradable rate that is faster than the degradable rate of the metal scaffold. In this case, the biodegradable polymer coating dissolves more rapidly than the metal scaffold after implantation. Preferably, the biodegradable polymer coating will cover the entire biodegradable metal scaffold long enough for the device to be fully encapsulated in the tissue so that the metal scaffold is degraded while encapsulated in the tissue, thus avoiding the possibility of releasing metal fragments into a body lumen during degradation. In certain embodiments, the metal scaffold is coated with a biodegradable polymer coating that degrades in one week, two weeks, three weeks, four weeks, two months, 3 months, 4 months, 6 months, 8 months, 12 months, 15 months, 18 months, or 2 years after implantation.

In certain embodiments, the polymer coating is a multi-layer coating comprising layers differing by their rate of degradation. In some embodiments, the fast degrading layer is an outer layer comprises a faster degrading layer and an inner layer comprises a slower degrading layer. In other embodiments, the faster degrading layer is an inner layer and the slower degrading layer is an outer layer.

In some embodiments, the faster degrading layer further comprises a bioactive agent, such as one that prevents or reduces the post-implantation hyperplastic response. Examples of such bioactive agents include small molecule drugs, large molecule drugs or biologics, collagenous extracellular matrix (ECM) materials, gene transfer vectors or cells as further described below. The slower degrading layer may contain the same agent or a different agent.

In some embodiments, the fast degrading layer is an outer layer comprising fissures so that body fluids may contact the slow degrading inner layer before the degradation of the outer layer. In the case of an expandable in vivo supporting device, the coating can be made of an elastic polymer composition to allow expansion of the biodegradable metal scaffold while maintaining the integrity of the coating. In another embodiment, the coating is made of a brittle composition that forms fissures when the metal scaffold expands so as to allow simultaneous degradation of both the coating and the metal scaffold. The required elasticity may be achieved using a mixture of crystalline and amorphous polymers, or co-polymers containing both amorphous segments and crystalline segments. For example, poly-D-lactide is amorphous and elastic, while poly-L-lactide has a higher level of crystallinity and is more brittle. A copolymer made of D- and L-lactide would be have an elasticity somewhere in between poly-D-lactide and poly-L-lactide.

In some embodiments, the one or more materials comprising the body, or the stent, or the tubular body may have a predefined crystallinity. As used herein, the term "crystallinity" refers to a degree of structural order or perfection within the polymer coating as measured by e.g., differential scanning calorimetry in accordance known measurement protocols, such as ASTM STP 1402. In some embodiments, the crystallinity of the polymeric coating is less than 50%, less than 40%, less than 35%, less than 30%, less than 25%, less than 20%, less than 15%, less than 10%, less than 5%, less than 2% or a range between any two integer values corresponding to the crystallinity values described herein. In other embodiments, the polymeric material has a crystallinity of greater than 2%, greater than 5%, greater than 10%, greater than about 15%, greater than about 20%, greater than about 25%, greater than about 30%, greater than about 35%, greater than 40%, greater than 50%, or a range between any two integer values corresponding to the crystallinity values described herein.

In certain embodiments, the fast degrading outer layer is degradable within 1 day, 2 days, 3 days, 4 days, 5 days, 6 days, 1 week, 2 week, 3 weeks, 4 weeks and the slow degrading inner layer is degradable within 1 week, 2 week, 3 weeks, 4 weeks, 2 months, 3 months, 4 months, 6 months, 1 year or 2 years.

The thickness of the outer and inner layers may be adjusted to achieve a desired level of degradation. In certain embodiments, the thickness of each layer is in the range of 10 μm to 200 μm. In devices with a metal scaffold having very thin struts, the total thickness of the outer and inner coating layers may range from 10 μm to 100 μm. In some embodiments, the outer and/or inner coating layer has an uneven thickness.

In another embodiment, the biodegradable polymer coating is permeable to body fluid to allow simultaneous degradation of both the coating and the metal scaffold after implantation. The permeability of the biodegradable polymer coating may be created by using a porous polymer coating/covering or by creating fissures or holes in the polymer coating/covering during the manufacturing process.

In other embodiments, the in vivo supporting device comprises an elastic polymer coating so that it can be used in non-conforming lesions. In some embodiments, the elastic polymer is mixed with metal particles that allow the material to be more malleable so that they can be crimped on the stent and retain its dilated form. Examples of such metal particles include, but are not limited to, particles of iron, magnesium, tantalum, zinc and alloys thereof. The metal particles can be of varying sizes and shapes. In certain embodiments, the metal particles are nanoparticles. The coating would have different linked structure and arrangement after crimping or expansion to keep the device compressed or open.

In some embodiments, the biodegradable polymer coating is mixed with, embedded with, or configured to carry, various agents, such as drugs, cells, or extracellular matrix (ECM) materials distributed uniformly throughout the coating. In other embodiments, the agents may be distributed non-uniformly throughout the coating. In yet other embodiments, the agents may be incorporated into the coating and/or the metal scaffold.

Exemplary agents that can be mixed with, embedded into or carried by the biodegradable polymer coating, scaffold, or both, include, but are not limited to, small molecule drugs, including anti-proliferative agents, chemotherapeutic agents and antimicrobial agents; large molecule drugs (i.e., biologics), such as antibodies; collagenous extracellular matrix (ECM) materials, gene transfer vectors, and cells include, but are not limited to, stem cells, harvested cells, genetically modified cells secreting bioactive agents, and the like.

Small molecule drugs include a wide ranging group of active organic compounds, including, but are not limited to, anti-proliferative agents, chemotherapeutic agents, and antimicrobial agents. Anti-proliferative agents include anti-restenosis agents, which inhibit the proliferation of smooth muscle cells that would otherwise lead to the reocclusion of an extended vessel. Exemplary anti-proliferative agents include paclitaxel, rapamycin (sirolimus), docetaxel, biolimus A9, zotarolimus, everolimus, myolimus, novolimus, pimecrolimus, tacrolimus, ridaforolimus and temsirolimus.

The chemotherapeutic agents include e.g., cis-platinum, 5-fluorouracal, gemcytobine and navelbine, and may be grouped as DNA-damaging agents, antimetabolites, tubulin-interactive agents, hormonal agents, hormone-related agents, and others such as asparaginase or hydroxyurea. Examples of DNA-damaging agents include, but are not limited to, alkylating agents, DNA strand-breakage agents; intercalating and nonintercalating topoisomerase II inhibitors, and DNA minor groove binders. Alkylating agents generally react with a nucleophilic atom in a cellular constituent, such as an amino, carboxyl, phosphate, or sulfhydryl group in nucleic acids, proteins, amino acids, or glutathione. Examples of alkylating agents include, but are not limited to, nitrogen mustards, such as chlorambucil, cyclophosphamide, isofamide, mechlorethamine, melphalan, uracil mustard; aziridines, such as thiotepa; methanesulfonate esters such as busulfan; nitroso, ureas, such as cannustine, lomustine, streptozocin; platinum complexes, such as cisplatin, carboplatin; bioreductive alkylator, such as mitomycin, and procarbazine, dacarbazine and altretamine. DNA strand breaking agents include, but are not limited to, bleomycin. Intercalating DNA topoisomerase II inhibitors include, but are not limited to, intercalators such as amsacrine, dactinomycin, daunorubicin, doxorubicin, idarubicin, and mitoxantrone. Nonintercalating DNA topoisomerase II inhibitors include, but are not limited to etoposide and teniposide. DNA minor groove binders include, but are not limited to, plicamycin. Antimetabolites interfere with the production of nucleic acids by one or the other of two major mechanisms. Some of the drugs inhibit production of the deoxyribonucleoside triphosphates that are immediate precursors for DNA synthesis, thus inhibiting DNA replication. Some of the compounds, for example, purines or pyrimidines, are sufficient to be able to substitute for them in the anabolic nucleotide pathways. These analogs can then be substituted into the DNA and RNA instead of their normal counterparts. The antimetabolites useful herein include: folate antagonists such as methotrexate and trimetrexate pyrimidine antagonists, such as fluorouracil, fluorodeoxyuridine, CB3717, azacytidine, cytarabine, and floxuridine purine antagonists include mercaptopurine, 6-thioguanine, fludarabine, pentostatin; sugar modified analogs include cytarabine and fludarabine; ribonucleotide reductase inhibitors include hydroxyurea. Tubulin interactive agents act by binding to specific sites on tubulin, a protein that polymerizes to form cellular microtubules. Microtubules are critical cell structure units. When the interactive agents bind on the protein, the cell cannot form microtubules tubulin interactive agents including vincristine and vinblastine, both alkaloids and paclitaxel.

Anti-hormonal agents include estrogens, conjugated estrogens and ethinyl estradiol and diethylstilbestrol, chlorotrianisene and idenestrol; progestins, such as hydroxyprogesterone caproate, medroxyprogesterone, and megestrol; androgens such as testosterone, testosterone propionate; fluoxymesterone, methyltestosterone; adrenal corticosteroids are derived from natural adrenal cortisol or hydrocortisone; prednisone, dexamethasone, methylprednisolone, and prednisolone; leutinizing hormone releasing hormone agents, gonadotropin-releasing hormone antagonists and anti-hormonal agents, antiestrogenic agents such as tamoxifen, antiandrogen agents, such as flutamide; antiadrenal agents such as mitotane and amminoglutethimide.

Hydroxyurea appears to act primarily through inhibition of the enzyme ribonucleotide reductase. Asparaginase is an enzyme that converts asparagine to nonfunctional aspartic acid and can block protein synthesis in tumors.

Each of the groups of chemotherapeutic agents can be further divided by type of activity or compound. For a detailed discussion of the chemotherapeutic agents and their method of administration, see Don, et al, Cancer Chemotherapy Handbook, 2d edition, pages 15-34, Appleton & Lange (Connecticut, 1994), herein incorporated by reference.

As used herein, the term "antimicrobial agent" refer to antibiotics, antiseptics, disinfectants, and combinations thereof, that are soluble in organic solvents such as alcohols, ketones, ethers, aldehydes, acetonitrile, acetic acid, formic acid, methylene chloride and chloroform. Classes of antibiotics include tetracyclines (e.g., minocycline), rifamycins (e.g., rifampin), macrolides (e.g., erythromycin), penicillins (e.g., nafcillin), cephalosporins (e.g., cefazolin), other β-lactam antibiotics (imipenem, aztreonam), aminoglycosides (e.g., gentamicin), chloramphenicol, sulfonamides (e.g., sulfamethoxazole), glycopeptides (e.g., vancomycm), quinolones (e.g., ciprofloxacin), fusidic acid, trimethoprim, metronidazole, clindamycin, mupirocin, polyenes (e.g., amphotericin B), azoles (e.g., fluconazole) and β-lactam inhibitors (e.g., sulbactam).

Specific antibiotics include minocycline, rifampin, erythromycin, nafcillin, cefazolin, imipenem, aztreonam, gentamicin, sulfamethoxazole, vancomycin, ciprofloxacin, trimethoprim, metronidazole, clindamycin, teicoplanin, mupirocin, azithromycin, clarithromycin, ofloxacin, lomefloxacin, norfloxacin, nalidixic acid, sparfloxacin, pefloxacin, amifloxacin, enoxacin, fleroxacin, temafloxacin, tosufloxacin, clinafloxacin, sulbactam, clavulanic acid, amphotericin B, fluconazole, itraconazole, ketoconazole and nystatin. Other examples of antibiotics, such as those listed in U.S. Pat. No. 4,642,104, herein incorporated by reference, will readily suggest themselves to those of ordinary skill in the art. Exemplary antiseptics and disinfectants include thymol, a-terpineol, methylisothiazolone, cetylpyridinium, chloroxylenol, hexachlorophene, cationic biguanides (e.g., chlorhexidine, cyclohexidine), methylenechloride, iodine and iodophores (e.g., povidone-iodine), triclosan, furanmedical preparations (e.g., nitrofurantoin, nitrofurazone), methenamine, aldehydes (e.g., glutaraldehyde, formaldehyde) and alcohols. Other examples of antiseptics and disinfectants will readily suggest themselves to those of ordinary skill in the art.

Remodelable collagenous extracellular matrix (ECM) materials include decellularized animal tissues, including tissue layers thereofrom and lyophilized powders therefrom, whereby "decellularized" refers to a state of the ECM tissue in which all or substantially all of the cells native to the ECM tissue have been removed. ECM materials provide a remodelable matrix or support for the growth of new tissue thereon. Common events during this remodeling process include: widespread neovascularization, proliferation of granulation mesenchymal cells, biodegradation/resorption of implanted remodelable material, and absence of immune rejection. By this process, autologous cells from the body can replace the remodelable portions in the implantable device.

ECM materials can be obtained from a source tissue of a warm-blooded vertebrate animal, such as an ovine, bovine or porcine animal. The source tissue layer is preferably a nonmineralized (i.e., soft tissue) source tissue. Suitable ECM tissue include those comprising submucosa, renal capsule membrane, dermal collagen, dura mater, pericardium, amnion, abdominal fascia, fascia lata, serosa, peritoneum or basement membrane layers, including liver basement membrane. Suitable submucosa materials for these purposes include, for instance, intestinal submucosa including small intestinal submucosa, stomach submucosa, urinary bladder submucosa, and uterine submucosa. Submucosal ECM tissue materials can be obtained by harvesting such tissue sources and delaminating the submucosa-containing matrix from smooth muscle layers, mucosal layers, and/or other layers occurring in the tissue source. Porcine tissue sources are preferred sources from which to harvest ECM tissues, including submucosa-containing ECM tissues.

Gene transfer vectors are capable of introducing polynucleotides into cells. The polynucleotide may contain the coding sequence of a protein or a peptide, or a nucleotide sequence that encodes a siRNA or antisense RNA. Examples of gene transfer vectors include, but are not limited to, non-viral vectors and viral vectors. Non-viral vectors typically include a plasmid having a circular double stranded DNA into which additional DNA segments can be introduced. The non-viral vector may be in the form of naked DNA, polycationic condensed DNA linked or unlinked to inactivated virus, ligand linked DNA, and liposome-DNA conjugates. Viral vectors include, but are not limited to, retrovirus, adenovirus, adeno-associated virus (AAV), herpesvirus, and alphavirus vectors. The viral vectors can also be astrovirus, coronavirus, orthomyxovirus, papovavirus, paramyxovirus, parvovirus, picornavirus, poxvirus, or togavirus vectors.

The non-viral and viral vectors also include one or more regulatory sequences operably linked to the polynucleotide being expressed. A nucleotide sequence is "operably linked" to another nucleotide sequence if the two sequences are placed into a functional relationship. For example, a coding sequence is operably linked to a 5' regulatory sequence if the 5' regulatory sequence can initiate transcription of the coding sequence in an in vitro transcription/translation system or in a host cell. "Operably linked" does not require that the DNA sequences being linked are contiguous to each other. Intervening sequences may exist between two operably linked sequences.

In one embodiment, the gene transfer vector encodes a short interfering RNA (siRNA). siRNAs are dsRNAs having 19-25 nucleotides. siRNAs can be produced endogenously by degradation of longer dsRNA molecules by an RNase III-related nuclease called Dicer. siRNAs can also be introduced into a cell exogenously or by transcription of an expression construct. Once formed, the siRNAs assemble with protein components into endoribonuclease-containing complexes known as RNA-induced silencing complexes (RISCs). An ATP-generated unwinding of the siRNA activates the RISCs, which in turn target the complementary mRNA transcript by Watson-Crick base-pairing, thereby cleaving and destroying the mRNA. Cleavage of the mRNA takes place near the middle of the region bound by the siRNA strand. This sequence specific mRNA degradation results in gene silencing. In another embodiment, the gene transfer vector encodes an antisense RNA.

Manufacture of the In Vivo Supporting Device

The in vivo supporting device can be laser cut, water jet cut, stamped, molded, lathed, 3D-printed or formed using any method commonly used in the art. In one embodiment, the scaffold is cut from a single metal tube. The tube may be hollow or the center may be cored out at varying diameters suitable for the particular indication. The scaffold may then etched and formed on a suitable shaping device to give the scaffold the desired external geometry. The formed scaffold is then coated with the biodegradable polymer coating using methods well known in the art.

As described above, the in vivo supporting device may be modified to control the rate of degradation. In one embodiment, the scaffold is first coated with a slow degrading inner coating and then coated with a fast degrading outer coating. In another embodiment, the scaffold is first coated with a fast degrading inner coating and then coated with a slow degrading outer coating.

In some embodiments, surface treatment of the metal scaffold by calcium phosphate treatment may be employed to reduce the rate of degradation. Other methodologies for controlling the rate of degradation include hydrofluoric acid treatment, alkaline-heat treatment and physical vapor deposition of high-purity Mg.

In certain embodiments, the in vivo supporting device is formed in such a way as to allow fluid flow to change in the pitch of the flow to improve flow dynamics and to speed the flow of fluids throughout the device. For example, the device may be formed to change from a tight radial design to a more longitudinal design.

In one embodiment, spiral surface channels with large cross-section areas are formed to accommodate large volumes of body fluid. In another embodiment, multiple channels with small cross-section area are formed to accommodate large volumes of body fluid. In another embodiment, the device body contains a large center lumen to allow for fluid flow and a plurality of small cross-section area channels on the surface to stabilize the device in vivo.

In another embodiment, the lips of the channel walls are tapered to increase the surface area for fluid flow and grip. Changes in the depth of the pitch of the channels will also have an impact on fluid flow and stability.

In one embodiment, the metal scaffold is formed on a shaping tool that has substantially the desired contour of the external stent dimensions. In the event the device is to be shaped to the dimensions of a particular lumen, optical photography and/or optical videography of the target lumen may be conducted prior to stent formation. The geometry of corresponding zones and connector regions of the metal scaffold then can be etched and formed in accordance with the requirements of that target lumen. For example, if the topography of the biliary duct of a particular patient is captured optically and the appropriate dimension provided, a patient-specific in vivo supporting device can be engineered. These techniques can be adapted to other non-vascular lumens, but is particularly well suited for vascular applications where patient specific topography is a function of a variety of factors such as genetics, lifestyle, etc.

The in vivo supporting device of the present invention can accommodate a virtually unlimited number of characteristic combinations, as zones and segments within a zone can be modified by changing angles, segment lengths, segment thicknesses, pitch during the etching and forming stages of device engineering or during post formation processing and polishing steps. Moreover, by modifying the geometry, depth, and diameter of the channels between zones, additional functionality may be achieved, such as flexibility, increased fluid transport, and changes in friction.

Method of Using the In Vivo Supporting Device

The in vivo supporting device of the present invention may be implanted with procedures known to persons of ordinary skill in the art. Exemplary deployment procedures include, but are not limited to, standard percutaneous deployment using a guide wire, endoscopic retrograde cholangiopancreatography (ERCP) placement, and other radiographic/angiographic procedures.

Another aspect of the present application relates to a method for treating a condition in a subject with a biodegradable in vivo supporting device, comprising: establishing an entry portal into a body lumen in a subject in need of such treatment; delivering the supporting device to a target location through said body lumen; and deploring the supporting device at the target location, wherein the biodegradable in vivo supporting device comprises a biodegradable metal alloy scaffold comprising a plurality of metal struts and a biodegradable polymer coating at least partially covering the metal struts. In some embodiments, the body lumen is a blood vessel. In some embodiments, the blood vessel is a cardiac blood vessel. In some embodiments, the metal struts have an average cross-sectional thickness between 100-200 µm, the polymer coating has a thickness between 10-100 µm.

Kits Comprising the In Vivo Supporting Device

Another aspect of the present application relates to a kit for placement of the biodegradable in vivo supporting device of the present application. In some embodiments, the kit comprises a biodegradable biodegradable in vivo supporting device comprising a biodegradable metal alloy scaffold comprising a plurality of metal struts and a biodegradable polymer coating at least partially covering the metal struts, and a guide wire.

In some embodiments, the biodegradable metal alloy scaffold comprises a magnesium alloy, an iron alloy, a zinc alloy, or combination thereof. In some embodiments, the metal alloy further comprises one or more metals selected from the group consisting of manganese, magnesium, neodymium, cerium, iron, zinc, palladium, cobalt, aluminum, tungsten, boron, carbon, sulfur, silicon, lithium, zirconium, calcium, and yttrium.

In some embodiments, the metal alloy further comprises at least one rare earth metal and a majority of the metal alloy comprises magnesium. In some embodiments, the rare earth metal is neodymium or cerium.

In some embodiments, the biodegradable metal scaffold is made from a magnesium alloy having at least 96 wt. % of magnesium, at least 1 wt. % of manganese, and at least 0.5 wt. % of a rare earth metal.

In some embodiments, the biodegradable metal scaffold is made from a magnesium alloy having a magnesium content of 96-97.9 wt. %, a manganese content of 1.6-2 wt. %, and rare earth metal content of 0.5-2 wt. %.

In some embodiments, the biodegradable metal scaffold is made from a magnesium alloy having a magnesium content of 97.45 wt. %, a manganese content of 1.8 wt. %, and a neodymium content of 0.75 wt. %.

In some embodiments, the biodegradable metal scaffold is an expandable scaffold. In some embodiments, the metal scaffold is less than 60% w/w or less than 60% v/v of the device.

In some embodiments, the biodegradable polymer coating is permeable to body fluid. In some embodiments, the biodegradable polymer comprises PLLA, PLGA, or a combination thereof.

In some embodiments, the biodegradable polymer coating has one or more holes allowing direct contact between the metal struts and body fluids when the stent device is placed inside a body lumen.

In some embodiments, the biodegradable polymer coating comprises an anti-proliferative agent selected from the group consisting of paclitaxel, sirolimus, docetaxel, biolimus A9, zotarolimus, everolimus, myolimus, novolimus, pimecrolimus, tacrolimus, ridaforolimus, temsirolimus and combination thereof.

In some embodiments, the supporting device further comprises an additional coating between the metal alloy scaffold and the biodegradable coating that delays the degradation time of the metal alloy scaffold. In some embodiments, the additional coating is a nano-coating of iron.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary.

What is claimed is:

1. A biodegradable balloon-expandable in vivo supporting device, comprising:
   a biodegradable metal alloy scaffold made from an alloy comprising magnesium, manganese and at least one rare earth metal, the scaffold comprising a plurality of metal struts; and
   a biodegradable polymer coating at least partially covering the metal struts,
   wherein coated struts have a cross-sectional width between 100-600 µm, the polymer coating has a thickness between 10-100 µm,
   wherein the metal alloy scaffold includes at least one rare earth metal, and
   wherein the metal scaffold comprises a cylinder-shaped stent body consisting of a plurality of axially arranged rows of struts encircling a central lumen in a wave pattern, wherein each row is configured in a substantially antiparallel arrangement relative to its adjacent row(s), and wherein each row is solely connected to an adjacent row by a plurality of curved connectors.

2. The device of claim 1, wherein the biodegradable metal alloy scaffold comprises a magnesium alloy, an iron alloy, a zinc alloy, or combination thereof.

3. The device of claim 2, wherein the alloy further comprises one or more metals selected from the group consisting of manganese, magnesium, neodymium, cerium, iron, zinc, palladium, cobalt, aluminum, tungsten, boron, carbon, sulfur, silicon, lithium, zirconium, calcium, and yttrium.

4. The device of claim 1, wherein the at least one rare earth metal is neodymium or cerium.

5. The device of claim 1, wherein the biodegradable metal scaffold is made from a magnesium alloy having at least 96 wt. % of magnesium, at least 1 wt. % of manganese, and at least 0.5 wt. % of a rare earth metal.

6. The device of claim 5, wherein the biodegradable metal scaffold is made from a magnesium alloy having a magnesium content of 96-97.9 wt. %, a manganese content of 1.6-2 wt. %, and rare earth metal content of 0.5-2 wt. %.

7. The device of claim 5, wherein the biodegradable metal scaffold is made from a magnesium alloy having a magnesium content of 97.45 wt. %, a manganese content of 1.8 wt. %, and a neodymium content of 0.75 wt. %.

8. The device of claim 1, wherein the alloy further comprises zirconium.

9. The device of claim 1, wherein the biodegradable polymer coating is permeable to body fluid.

10. The device of claim 1, wherein the biodegradable polymer comprises PLLA, PLGA, or a combination thereof.

11. The device of claim 1, wherein the biodegradable polymer coating has one or more holes allowing direct contact between the metal struts and body fluids when the stent device is placed inside a body lumen.

12. The device of claim 1, wherein the biodegradable polymer coating comprises an anti-proliferative agent selected from the group consisting of paclitaxel, sirolimus, docetaxel, biolimus A9, zotarolimus, everolimus, myolimus, novolimus, pimecrolimus, tacrolimus, ridaforolimus, temsirolimus and combination thereof.

13. The device of claim 1, further comprising an additional coating between the metal alloy scaffold and the biodegradable coating that delays the degradation time of the metal alloy scaffold.

14. The device of claim 13, wherein the additional coating is a nano-coating of iron.

15. A biodegradable balloon-expandable in vivo supporting device, comprising:
   a biodegradable metal alloy scaffold made from a magnesium alloy, an iron alloy, a zinc alloy, or combination thereof, the metal scaffold comprising a plurality of metal struts;
   a biodegradable polymer coating at least partially covering the metal struts,
   wherein the magnesium alloy, iron alloy, and/or zinc alloy has a manganese content of at least 1 wt. %, and
   wherein coated struts have a cross-sectional width between 100-600 µm, the polymer coating has a thickness between 10-100 µm, and
   wherein the metal scaffold comprises a cylinder-shaped stent body consisting of a plurality of axially arranged rows of struts encircling a central lumen in a wave pattern, wherein each row is configured in a substantially antiparallel arrangement relative to its adjacent row(s), and wherein each row is solely connected to an adjacent row by a plurality of curved connectors.

16. A biodegradable balloon-expandable in vivo supporting device, comprising:
   a biodegradable metal alloy scaffold made from a magnesium alloy including magnesium, manganese, and neodymium or cerium, the metal scaffold comprising a plurality of metal struts; and
   a biodegradable polymer coating at least partially covering the metal struts, coated struts have a cross-sectional width between 100-600 µm, the polymer coating has a thickness between 10-100 µm, and
   wherein the metal scaffold comprises a cylinder-shaped stent body consisting of a plurality of axially arranged rows of struts encircling a central lumen in a wave pattern, wherein each row is configured in a substantially antiparallel arrangement relative to its adjacent row(s), and wherein each row is solely connected to an adjacent row by a plurality of curved connectors.

17. A kit for placement of the biodegradable in vivo supporting device of claim 1, further comprising:
   a guide wire, and
   a setting bulb that maximizes a diameter of the biodegradable metal alloy scaffold and sets the in biodegradable vivo supporting device in place.

18. The device of claim 15, wherein the alloy further comprises zirconium.

19. The device of claim 16, wherein the alloy further comprises zirconium.

* * * * *